(12) United States Patent
Schneider et al.

(10) Patent No.: US 9,987,389 B2
(45) Date of Patent: Jun. 5, 2018

(54) ARTICLES WITH ODOR-CONTROLLING COMPOSITION

(71) Applicant: Rem Brands, Inc., Walton, KY (US)

(72) Inventors: David J. Schneider, Union, KY (US); Laura G. Kiely, Hebron, KY (US)

(73) Assignee: REM BRANDS, INC., Walton, KY (US)

( * ) Notice: Subject to any disclaimer, the term of this patent is extended or adjusted under 35 U.S.C. 154(b) by 0 days. days.

(21) Appl. No.: 15/019,879

(22) Filed: Feb. 9, 2016

(65) Prior Publication Data

US 2016/0158404 A1    Jun. 9, 2016

Related U.S. Application Data

(63) Continuation-in-part of application No. 13/105,954, filed on May 12, 2011, now Pat. No. 9,539,446.

(Continued)

(51) Int. Cl.
*A61K 8/46*  (2006.01)
*A61L 15/46*  (2006.01)

(Continued)

(52) U.S. Cl.
CPC .............. *A61L 15/46* (2013.01); *A61K 8/466* (2013.01); *A61Q 19/00* (2013.01); *B01J 20/22* (2013.01);

(Continued)

(58) Field of Classification Search
None
See application file for complete search history.

(56) References Cited

U.S. PATENT DOCUMENTS 4,857,065 A * 8/1989 Seal .................... A61F 13/533
                                                       428/213
6,296,841 B1  10/2001 Schneider
(Continued)

FOREIGN PATENT DOCUMENTS

EP       1 034 799 A1   9/2000
WO   WO 2011/143376 A1   11/2011

OTHER PUBLICATIONS

International Search Report and Written Opinion for International Application No. PCT/US2016/017206 dated May 9, 2016.

*Primary Examiner* — Aradhana Sasan
(74) *Attorney, Agent, or Firm* — Richard M. Klein; Fay Sharpe LLP

(57) ABSTRACT

Articles are treated with a reduced amount of a halo active aromatic sulfonamide compound of Formula (I):

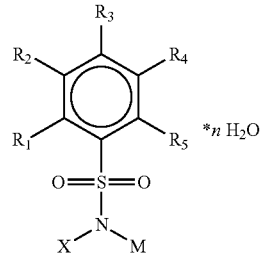

Formula (I)

wherein $R_1$, $R_2$, $R_3$, $R_4$, and $R_5$ are independently selected from hydrogen, COOR', CON(R'')$_2$, alkoxy, CN, NO$_2$, SO$_3$R'', halogen, substituted or unsubstituted phenyl, sulfonamide, halosulfonamide, and substituted or unsubstituted $C_1$-$C_{12}$ alkyl; R' is hydrogen, an alkali metal, an alkaline (Continued)

earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected; X is halogen; M is an alkali or alkaline earth metal; and n is the number of water molecules per molecule of the sulfonamide compound. The compound effectively suppresses odors pre-use, in use, and post-use for extended periods of time.

19 Claims, 10 Drawing Sheets

Related U.S. Application Data

(60) Provisional application No. 62/113,768, filed on Feb. 9, 2015, provisional application No. 61/334,678, filed on May 14, 2010.

(51) Int. Cl.
*A61Q 19/00* (2006.01)
*B01J 20/00* (2006.01)
*A61Q 17/04* (2006.01)
*A61Q 5/02* (2006.01)
*A61Q 5/06* (2006.01)
*B01J 20/22* (2006.01)

(52) U.S. Cl.
CPC ............ *A61K 2800/10* (2013.01); *A61Q 5/02* (2013.01); *A61Q 5/06* (2013.01); *A61Q 17/04* (2013.01)

(56) References Cited

U.S. PATENT DOCUMENTS

| | | | |
|---|---|---|---|
| 7,465,829 B2 * | 12/2008 | Schneider | A01N 41/06 558/413 |
| 8,425,890 B2 * | 4/2013 | Schneider | A61F 13/8405 424/431 |
| 9,539,446 B2 * | 1/2017 | Schenider | A61K 8/466 |
| 2005/0287109 A1 | 12/2005 | Schneider et al. | |
| 2006/0280766 A1 * | 12/2006 | Schneider | A01N 41/08 424/405 |
| 2010/0215612 A1 | 8/2010 | Schneider et al. | |

* cited by examiner

ARTICLES WITH ODOR-CONTROLLING COMPOSITION

CROSS-REFERENCE TO RELATED APPLICATIONS

This application claims priority to U.S. Provisional Patent Application Ser. No. 62/113,768, filed on Feb. 9, 2015. This application is also a continuation-in-part of U.S. patent application Ser. No. 13/105,954, filed on May 12, 2011, which claims priority to U.S. Provisional Patent Application Ser. No. 61/334,678, filed May 14, 2010. The disclosure of these applications are hereby fully incorporated by reference herein.

BACKGROUND

The present disclosure relates to compounds having odor control characteristics.

Absorbent members, such as pads, find widespread use in absorbing body or bodily fluids in articles such as catamenial devices, diapers (both for babies and individuals with incontinence problems), sanitary napkins, tampons, wound dressings, and bandages. Such absorbent members may incorporate super absorbent polymers (which absorb many times their own weight of fluid) or other fibrous materials, such as cotton, wood pulp, and paper. The bodily fluids absorbed by such absorbent members may include vomit, blood, pus, sweat, semen, secretions, menstrual discharge, urine, and fecal matter.

The bodily fluid may have an unpleasant odor (malodor) due to odor-causing molecules which may be aliphatic, aromatic, or heterocyclic compounds containing oxygen, sulfur, or nitrogen. The odor-causing molecules can be masked using a more pleasant smelling molecule, such as a perfume. However, it would be desirable to alter, neutralize, and/or destroy the odor-causing molecule instead. It would also be beneficial to provide improved bodily fluid absorbent members having enhanced odor control properties. Particularly, it would be desirable to neutralize and/or destroy odor-causing molecules that are generated/released over an extended period of time, allowing for extended treated article wear and easy undetectable disposition of said article.

BRIEF DESCRIPTION

Disclosed herein, in various embodiments, are odor-controlling articles that can be used to absorb various bodily fluids. The odor-controlling articles include compositions comprising a halo active aromatic sulfonamide compound according to Formula (I), shown herein.

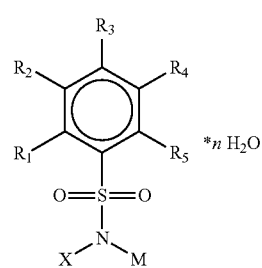

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound. The articles include a reduced amount of the sulfonamide compound compared to those previously described, such as from about 0.0002 to about 6 milligrams of the sulfonamide compound per milliliter (mg/mL) of absorbent capacity of the absorbent member.

In particular embodiments, $R_3$ is COOR'. In particular, R' is an alkali or alkaline earth metal. In still more embodiments, $R_3$ is methyl, COOH, or COOM$_1$, with the other R groups being hydrogen.

In yet more embodiments, $R_3$ is selected from COOH, COOM$_1$, COOR', CON(R")$_2$, CN, NO$_2$, halogen, and substituted or unsubstituted $C_2$-$C_{12}$ alkyl. The other R groups are usually hydrogen in those embodiments. In more specific embodiments, $R_3$ is selected from COOH, COOM$_1$, COOR', and CON(R")$_2$.

In particular embodiments, the sulfonamide compounds are of Formulas (III) or (IV):

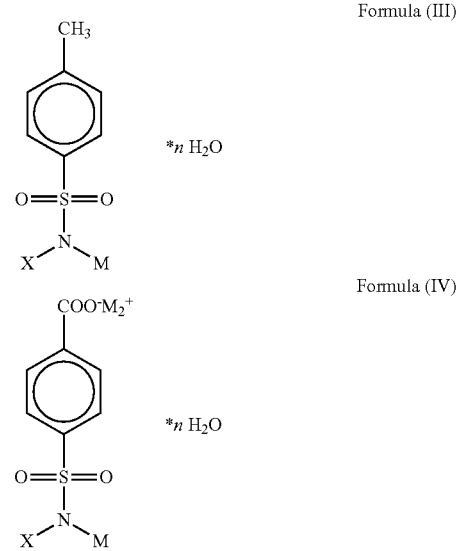

wherein $M_2$ is hydrogen, an alkali metal, or an alkali earth metal; X is halogen, M is independently an alkali or alkaline earth metal; and n is the number of water molecules per molecule of each sulfonamide compound.

In particular embodiments, a buffering agent is present as well, such as sodium bicarbonate. The weight ratio of the halo active aromatic sulfonamide compound to the buffering agent can be from about 50:1 to about 1:1. Alternatively, the buffering agent is present in a quantity sufficient to obtain a pH of 7.0 to 9.0 when the absorbent member is wetted (typically with urine, which is somewhat acidic).

In more embodiments, the halo active aromatic sulfonamide compound is encapsulated in a water-soluble shell.

This allows the sulfonamide to be released over time as the shell dissolves, enhancing the lifetime of the odor-controlling effect.

The halo active aromatic sulfonamide compound may be applied to an article in the form of an odor-controlling composition that also comprises a solvent. The halo active aromatic sulfonamide compound can be from about 0.1% to about 23% (w/v) of the composition, or from about 0.1% to 5% (w/v) of the composition, or from about 10% to about 20% (w/v) of the composition. The composition may have a pH of 7.0 to 9.0.

It is contemplated that the halo active aromatic sulfonamide compound may be in the form of a solid, which is dispersed on or within the absorbent substrate. For example, the absorbent substrate can be made of a super absorbent polymer.

Also disclosed is an article comprising: an absorbent substrate; and disposed thereon a halo active aromatic sulfonamide compound of Formula (I):

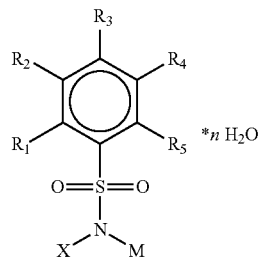

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound.

The absorbent substrate can be made from an absorbent material such as a polymer, a non-woven material, cellulosic fiber, or wood fluff. The absorbent substrate could be in the form of a flat sheet. The absorbent substrate may be used in a diaper, an adult incontinence article, a sanitary napkin, a tampon, a wound dressing, or a bandage, wipe, or a pad.

The weight ratio of the halo active aromatic sulfonamide compound to the absorbent substrate can be from about 0.001 to about 1.0 grams per gram of the absorbent substrate. The odor-controlling article can be made by treating the absorbent substrate with the odor controlling composition and then drying to obtain the odor-controlling article. The absorbent substrate can be treated by dipping, spraying, or washing.

Also disclosed are processes for reducing the odor of an odorific liquid for a time period of at least one week, comprising: receiving the odorific liquid in an article comprising an absorbent substrate having thereon a halo active aromatic sulfonamide compound of Formula (I):

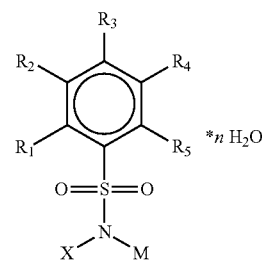

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound.

In particular, the odor of the liquid after one week may be at most 40% of the original odor, using a measuring system as explained herein.

Also contemplated are other deodorant or body odor products that use the odor-controlling composition comprising the sulfonamide compound of Formula (I). These use the same mechanism of odor control.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 2A is for a 46-year old female on an asparagus diet. FIG. 2B is for a 40-year old female on an asparagus diet. FIG. 2C is for a 30-year old female on a coffee diet. Odor was evaluated on a scale from 0 to 10 (y-axis), with 10 representing strong odor.

Discreet adult incontinence product. Odor was evaluated on a scale from 0 to 10 (y-axis), with 10 representing strong odor.

Figure 6:
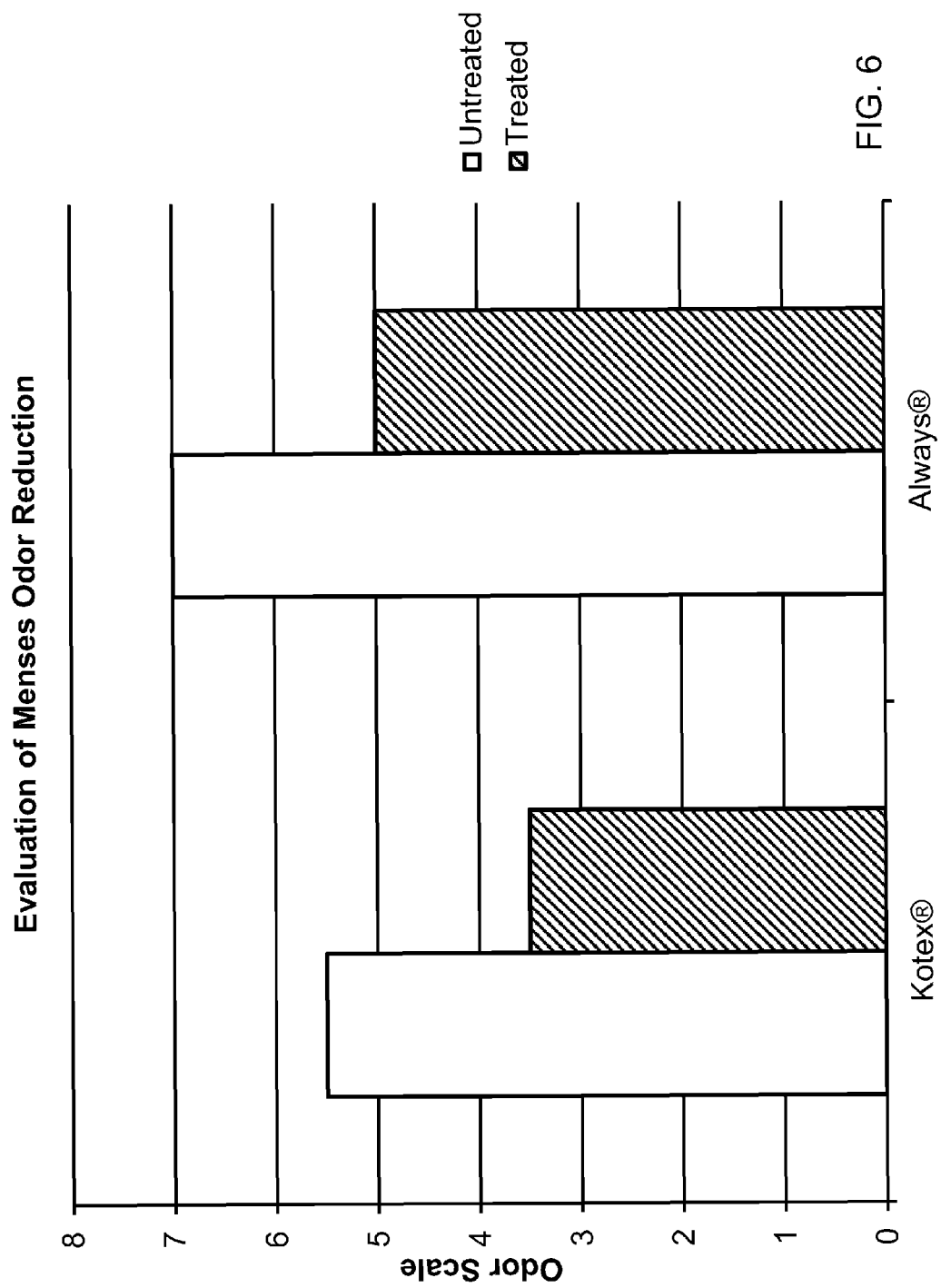

FIG. 6 is a graph comparing the odor reduction of the active sulfonamide compounds against a control for two different types of feminine pads.

Figure 7:
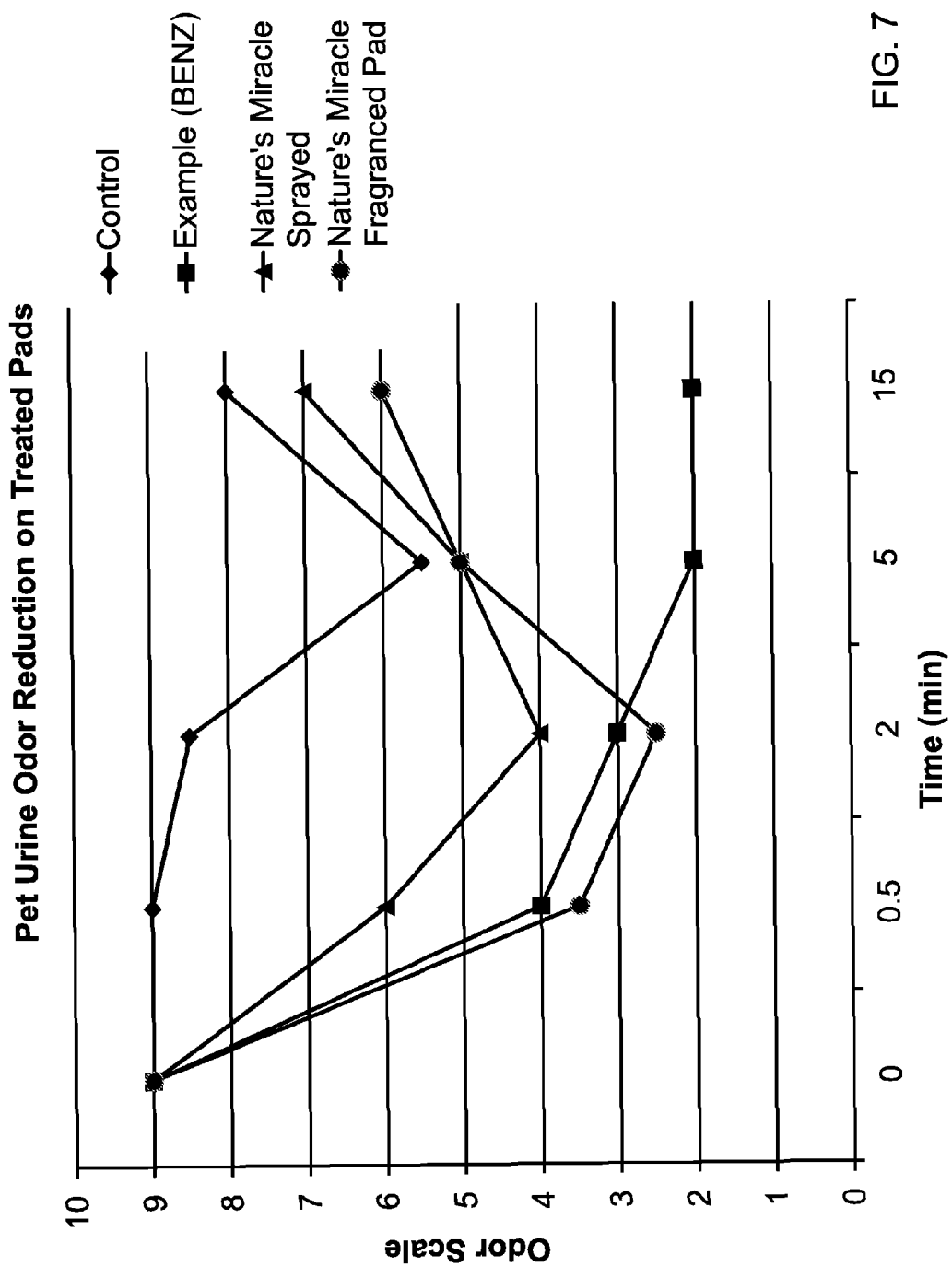

FIG. 7 is a graph comparing the odor reduction over time for three different treated pet pads, plus a fourth control pad, using different odor-controlling compositions.

Figure 8:
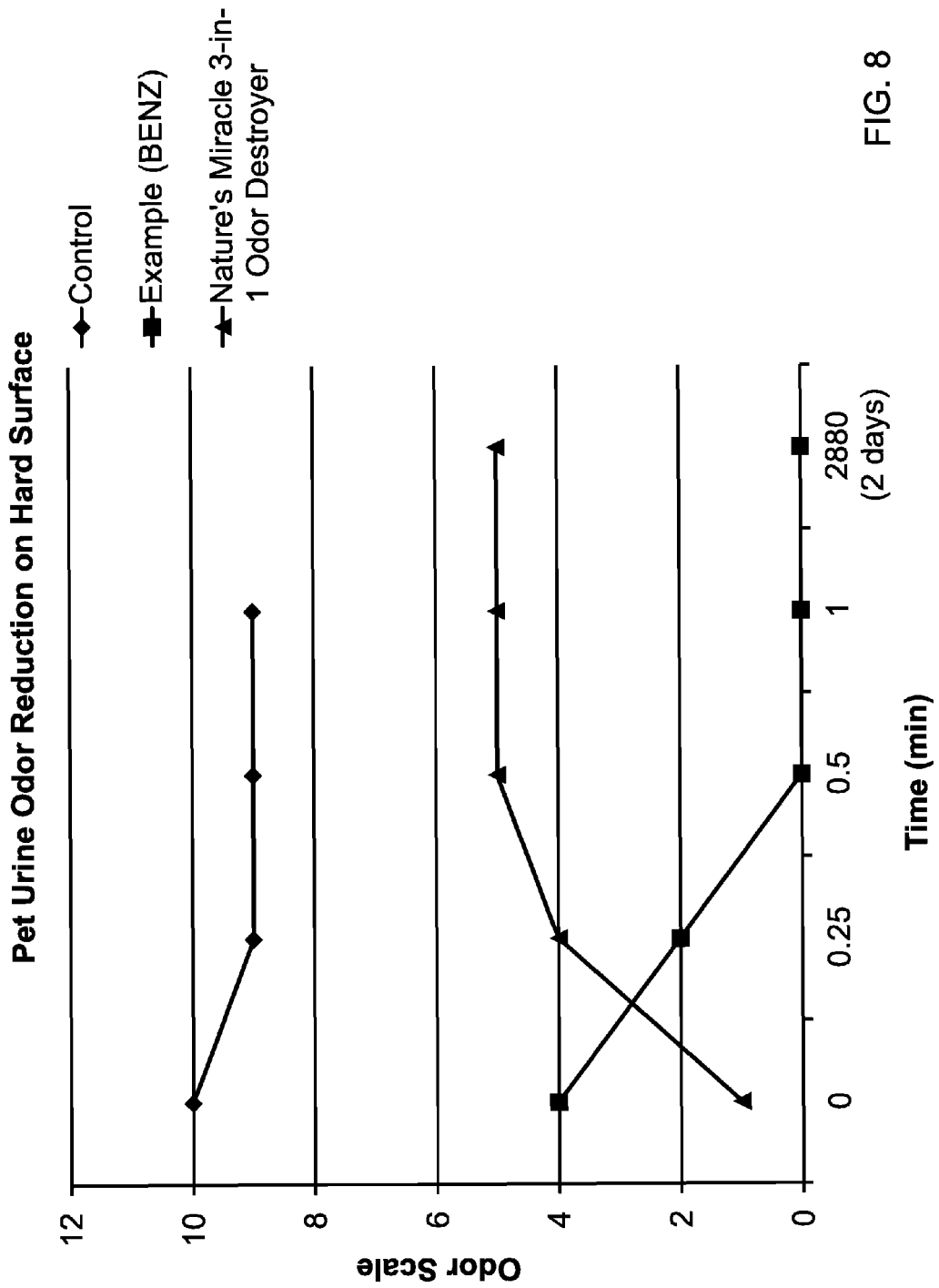

FIG. 8 is a graph comparing odor reduction over time for two different compositions (ODOGard® versus Nature's Miracle®).

DETAILED DESCRIPTION

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "article" is used to refer to an item or object, and should not be construed as limiting such items due to size. It is specifically contemplated that smaller items can be assembled to form a larger item, and both the small and large items will be referred to herein as "articles".

Halo active aromatic sulfonamide organic compounds are known. Chloramine-T is an example of a sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The active Cl+ ion and the companion aromatic sulfo nitrene ion may work together to degrade odor-causing molecules. The term "Cl+" refers to the fact that the chlorine atom has a +1 formal charge in a hypochlorite ion, $ClO^-$, which is the form taken by the chlorine atom when dissociated from the sulfonamide compound. A chlorine atom is generally considered to have a charge of $1^-$. Reference to the chlorine atom as having a +1 or $1^-$ charge may be used in this application interchangeably because this terminology has no effect on the compound itself or its use.

Most odor causing molecules are mercaptans, sulfides, heterocyclic or amine based compounds. Halo active aromatic sulfonamide compounds are excellent agents for eliminating odors from these classes of compounds as both the Cl+ cations and the sulfonamide moiety remaining after the Cl+ cations are produced, react with the odor causing molecule(s).

The odor-controlling articles of the present disclosure generally comprise (i) an absorbent member or substrate; and (ii) a halo active aromatic sulfonamide compound, as described further herein. The halo active aromatic sulfonamide compound can be applied to the absorbent member or substrate in the form of an odor-controlling composition, or in other words, the odor-controlling composition can be generally dispersed within or throughout the absorbent substrate. The absorbent substrate can be shaped as desired for its intended use/purpose/application. The absorbent member may be used in an article such as, for example, a diaper or other sanitary product.

The shape of the odor-controlling bodily fluid absorbent member can be varied depending on its use; for example, it can be made as a flat sheet or in a tubular form. It should be noted that the absorbent member is generally only one part of the overall consumer article.

Figure 1:
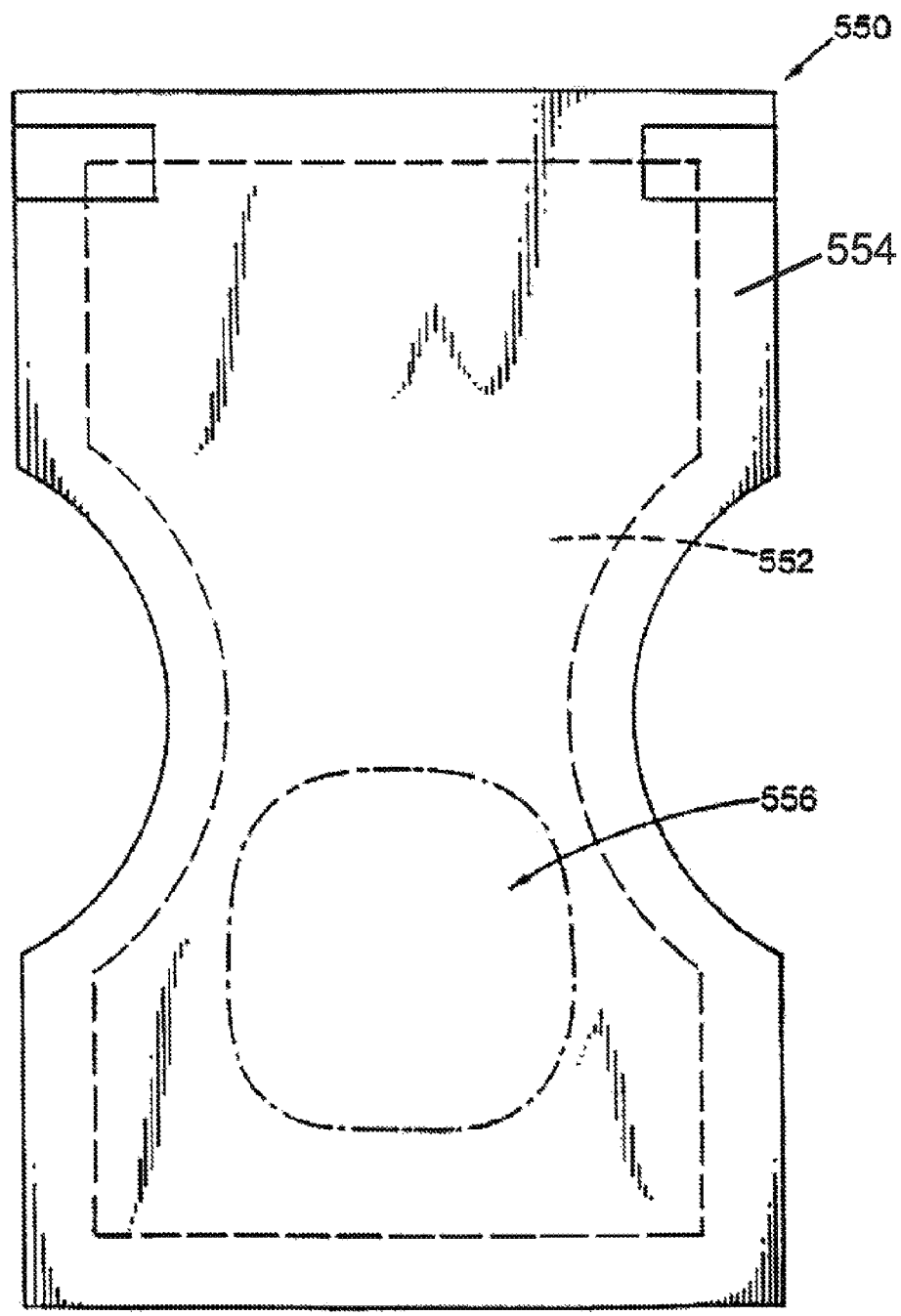
FIG. 1 is a top view of a diaper containing an absorbent member/substrate of the present disclosure.

For example, FIG. 1 illustrates a conventional disposable diaper 550. The diaper has two primary parts, a shell 554 and a core. The shell is the outermost layer of the diaper, and generally holds the core together and otherwise is used to fit the diaper to the user (e.g. an infant or an incontinent adult). The core is the portion of the diaper where urine is absorbed. The core includes a topsheet, an acquisition and distribution layer (ADL) 552, and an absorbent member 556. The topsheet contacts the skin. The ADL is designed to quickly move liquid away from the topsheet and distribute the liquid evenly across the absorbent member for better absorbency. The absorbent member 556 may be in the shape of a flat sheet, and can either be attached to the ADL/topsheet or to the shell. The absorbent member may be shaped as desired. If desired, a bottom sheet may also be included. The bottom sheet is impermeable to liquids and is intended to serve as a shield against leaks. Generally speaking, the absorbent member may be engaged with a housing to form a final article; here, the final article is a diaper. The article, such as a diaper, may also include other parts, such as a stretch laminate, an elastic film, a tab enclosure, or an adhesive. A stretch laminate is generally a multi-layer composite of elastic film with a soft nonwoven material. The stretch laminate or elastic film is generally used to form the waist-band of the diaper, or to make the band that secures the back of the diaper to the front of the diaper. The tab enclosure is the portion of the tape that actually secures the back of the diaper to the front of the diaper, and is attached to the band.

The absorbent member generally comprises an absorbent material. The absorbent material may be natural or synthetic. The absorbent material may also be in the form of fibers, powders, or granules, or in larger amounts in the form of sheets, mats, pads, or tubes. Exemplary absorbent materials generally include a mixture of (i) synthetic fibers made from polyacrylates (e.g. sodium polyacrylate), polyacrylamide copolymers, ethylene maleic anhydride copolymers, polyvinyl alcohol copolymers, cross-linked polyethylene oxide, or starch grafted copolymers of polyacrylonitrile; and (ii) cellulosic fibers such as cotton, rayon, and wood pulp. Many of the synthetic fibers (i) are also known as "super absorbent polymers" because they can absorb more than one hundred times their own weight of liquid. In specific embodiments, the absorbent material includes a "fluff" made by pulverizing sheets of wood pulp fibers. The absorbent material is generally a solid material when dry, and can be in powder, crystal, or particulate form.

The halo active aromatic sulfonamide compound used in the odor-controlling articles and with the absorbent members/substrates of the present disclosure has the structure of Formula (I):

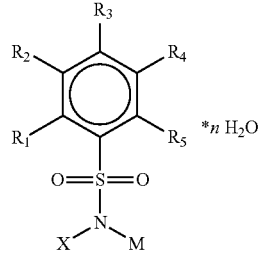

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

It should be noted that the term "aromatic", as used herein, refers to the chemical property of conjugated bonds whose delocalized electrons contribute to the stability of the overall compound and is not used to refer to a smell detected by the nose.

Generally, M is sodium or potassium. X is generally chlorine, bromine, fluorine, or iodine, and in particular embodiments is chlorine. Compounds of Formula (I) may or may not be hydrated, as indicated by the variable n. In particular embodiments, the compounds of Formula (I) are a trihydrate (i.e., n=3). In other embodiments, the compound is in a solid form, such as a powder.

R' is substituted or unsubstituted $C_1$-$C_{12}$ alkyl. R" is hydrogen or substituted or unsubstituted $C_1$-$C_{12}$ alkyl, and the two R" groups in the CON(R")$_2$ may be independently selected.

When the phenyl and/or alkyl group is substituted, one or more hydrogen atoms may be independently replaced with hydroxyl or halogen.

In some embodiments of Formula (I), at least two of $R_1$, $R_2$, $R_3$, $R_4$, and $R_5$ are not hydrogen.

In particular embodiments of Formula (I), $R_3$ is methyl, COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; X is halogen; M$_1$ is an alkali or alkaline earth metal; and n is the number of water molecules per molecule of the sulfonamide compound.

In further embodiments, $R_3$ is methyl, COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; X is halogen; M is an alkali or alkaline earth metal; n is the number of water molecules per molecule of the sulfonamide compound; and at least one of $R_1$, $R_2$, $R_4$, and $R_5$ is not hydrogen.

In other embodiments of Formula (I), the halo active aromatic sulfonamide compound has the structure of Formula (II):

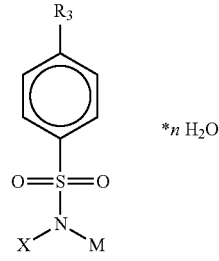

Formula (II)

wherein $R_3$ is COOR'; R' is hydrogen, an alkali metal, an alkaline earth metal, substituted $C_1$-$C_{12}$ alkyl, or unsubstituted $C_1$-$C_{12}$ alkyl; X is halogen; M is an alkali or alkaline earth metal; and n is the number of water molecules per molecule of the sulfonamide compound. The N-chloro-4-carboxybenzenesulfonamide compound of Formula (II) is also referred to herein as BENZ. BENZ exhibits a lower chlorine smell than chloramine-T or chloramine-B. When BENZ is combined with at least one fragrance, there is no detectable chlorine smell for most humans.

Two particular sulfonamide compounds contemplated for use are N-chloro-p-toluenesulfonamide (i.e. chloramine-T) and N-chloro-4-carboxybenzenesulfonamide (i.e. BENZ). These two compounds are shown below as Formulas (III) and (IV):

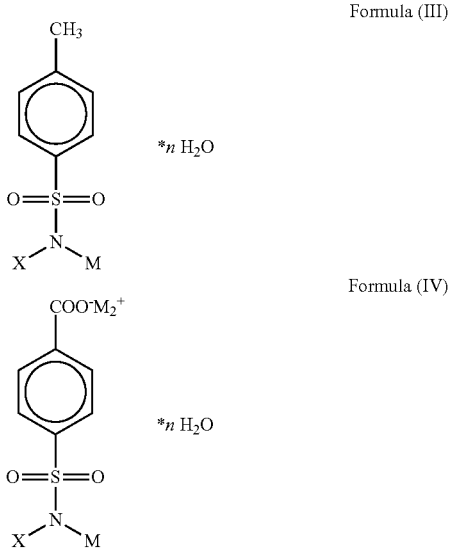

wherein M₂ is hydrogen, an alkali metal, or an alkali earth metal; X is halogen, M is independently an alkali or alkaline earth metal; and n is the number of water molecules per molecule of each sulfonamide compound. Desirably, M₂ is hydrogen, sodium, or potassium.

In yet other embodiments of Formula (I), $R_3$ is selected from COOH, COOM₁, COOR', CON(R")₂, CN, NO₂, halogen, and substituted or unsubstituted $C_2$-$C_{12}$ alkyl; $R_1$, $R_2$, $R_4$, and $R_5$ are independently selected from hydrogen, COOH, COOM₁, COOR', CON(R")₂, alkoxy, CN, NO₂, SO₃R", halogen, substituted or unsubstituted phenyl, sulfonamide, halosulfonamide, and substituted or unsubstituted $C_1$-$C_{12}$ alkyl; X is halogen; M is an alkali or alkaline earth metal; and n is the number of water molecules per molecule of the sulfonamide compound.

In still other embodiments of Formula (I), $R_1$, $R_2$, $R_3$, $R_4$, and $R_5$ are independently selected from hydrogen, COOH, COOM₁, NO₂, halogen, and substituted or unsubstituted $C_1$-$C_{12}$ alkyl; X is halogen; M is an alkali or alkaline earth metal; and n is the number of water molecules per molecule of the sulfonamide compound.

In yet other embodiments of Formula (I), $R_2$ and $R_4$ are identical to each other; and $R_1$, $R_3$, and $R_5$ are hydrogen.

In yet other embodiments of Formula (I), $R_2$ and $R_4$ are hydrogen; and $R_1$, $R_3$, and $R_5$ are identical to each other.

In more specific embodiments of Formula (I), $R_3$ is selected from COOH, COOM₁, COOR', and CON(R")₂. Most desirably, $R_3$ is COOH or COOM₁, while $R_1$, $R_2$, $R_4$, and $R_5$ are hydrogen.

In other embodiments of Formula (I), $R_1$, $R_2$, $R_3$, $R_4$, and $R_5$ are independently selected from hydrogen, COOH, COOM₁, COOR', CON(R")₂, NO₂, halogen, and substituted or unsubstituted $C_1$-$C_{12}$ alkyl; wherein at least one of $R_1$, $R_2$, $R_3$, $R_4$, and $R_5$ is not hydrogen; X is halogen; M is an alkali or alkaline earth metal; and n is the number of water molecules per molecule of the sulfonamide compound.

In still other embodiments of Formula (I), $R_3$ is COOH or COOM₁; $R_1$, $R_2$, $R_4$, and $R_5$ are independently selected from hydrogen, NO₂, halogen, and substituted or unsubstituted $C_1$-$C_{12}$ alkyl; X is halogen; M is an alkali or alkaline earth metal; and n is the number of water molecules per molecule of the sulfonamide compound. In further specific embodiments, at least one of $R_1$, $R_2$, $R_4$, and $R_5$ is not hydrogen.

The halo active aromatic sulfonamide compounds of Formula (I) are stable and do not decompose in aqueous solution, allowing the absorbent member to have a long shelf life. The compounds of Formula (I) are also very soluble in water, low in toxicity, and have minimal bleach odor.

The halo active aromatic sulfonamide compound can be present in the amount of about 0.0002 to about 6 milligrams per milliliter (mg/mL) of absorbent capacity of the absorbent member. As an example, if the absorbent member has a capacity of 100 mL, then 0.02 milligrams to 600 mg of the sulfonamide compound may be present. In further embodiments, the compound is present in the amount of about 0.0002 to about 1 mg/mL, or about 0.1 to about 1 mg/mL, or about 0.1 to about 0.5 mg/mL, or about 0.5 to about 1 mg/mL of absorbent capacity of the absorbent member. There may be a total of about 10 mg to about 3000 mg of the halo active aromatic sulfonamide compound in the absorbent member, or from about 10 mg to about 1000 mg, or from about 20 mg to about 1000 mg, or from about 40 mg to about 600 mg, or from about 100 mg to about 500, or from about 300 mg to about 400 mg. Put another way, the amount of the halo active aromatic sulfonamide compound can be from about 0.001 to about 1.0 wt % of the absorbent member, or from about 0.025 wt % to about 0.50 wt %, or from about 0.05 wt % to about 0.30 wt %. Again, it is particularly contemplated that the active sulfonamide compound is in the form of a dry solid powder.

For stability and for optimum performance, the pH of the odor-controlling composition should be between 6 and 14, though generally the pH should be kept between 7 and 9. As urine can have a pH ranging from 4.5 to 8, and is generally acidic, this pH range also helps to neutralize the urine collected in the absorbent member.

In order to maintain the solution within these pH ranges, a buffering agent may be present. The buffering agent can compensate for any change in pH that may result from the acidity of the urine, the conditions of application, the type of absorbent material or substrate, and/or the nature of the odor causing molecule. Exemplary buffering agents include sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate), and mixtures thereof. The buffering agent can be added up to the limit of solubility of the odor-controlling composition that is used to apply the halo active aromatic sulfonamide compound. In particular embodiments, the preferred weight ratio of the sulfonamide compound to the buffering agent is from about 50:1 to about 1:1, or from about 50:1 to about 2:1, or from about 20:1 to about 2:1. The preferred buffering agent is sodium bicarbonate.

The use of the bicarbonates in the disclosed compositions also appears to decrease color which may be due to pH effects. In particular, bicarbonates reduce the yellow color of BENZ solutions drastically. This effect may be highly desirable in some applications, such as diapers, pads, and similar applications where a yellow color is disfavored.

A fragrance can be included in the absorbent member/the odor-controlling article, if desired. The term "fragrance," as used herein, refers to one or more chemical compounds that, when combined with the halo active aromatic sulfonamide compound of Formula (I), produces an odor control composition that does not exhibit a strong smell.

Many different fragrances are known in the art. However, only certain fragrances result in a composition that does not exhibit a strong smell. In particular, it has been found that certain combinations of sulfonamide with fragrance which were expected to result in a composition without strong smell, did not perform as expected. The choice of the fragrance is critical and is not obvious.

Suitable fragrances are commercially available from manufacturers such as Givaudan and Horizon Aromatics. The following table of fragrances lists the name of some exemplary fragrances:

TABLE 1

| Fragrance Name |
| --- |
| Fabric Delight 1 |
| Lavender & Chamomile |
| Linen Basket |
| Outdoor Clean |
| Rain Garden GNF |
| Fragrance Duplicate A |
| Fragrance Duplicate B |

In this regard, it is known that the active compounds in lavender are linalool and linalyl acetate, and an active compound in chamomile is bisabolol. Thus, the fragrance may be selected from linalool, linalyl acetate, or bisabolol.

The fragrance may be present in an amount of from about 0.005 to about 5 wt % of the absorbent member. In some embodiments, the fragrance may be present in an amount of from about 0.01 to about 1 wt % of the absorbent member. In other embodiments, the fragrance may be present in an amount of from about 0.025 to about 0.5 wt %, or from about 0.05 to about 0.1 wt %, of the absorbent member.

A surfactant, or wetting agent, can also be added to the odor-controlling composition. The surfactant decreases surface tension, allowing the sulfonamide compound to be more easily activated when contacted by bodily fluids. Both non-ionic and anionic surfactants can be used. However, in specific embodiments, a surfactant is not used.

A low molecular weight alcohol may also be added to the odor-controlling composition to enhance the activity of the sulfonamide compound. An exemplary alcohol is t-butanol. The alcohol may have several effects. The alcohol enhances the odor removal activity of the active aromatic N-halo sulfonamide group. The alcohol can also increase surface activity or enable the use of a more favorable blend of fragrances, surface active compounds and the like. The type of alcohol used, however, is somewhat limited. T-butanol or related tertiary alcohols are preferred because they do not contain hydrogen atoms alpha to the oxygen alcohol moiety, and allow for greater stability. The alpha hydrogen atoms apparently detract from stability due to interaction with the active halogen contained in the active aromatic halo sulfonamide compound. However, in specific embodiments, an alcohol is not used.

In other embodiments, the sulfonamide compound is encapsulated. More specifically, the sulfonamide compound may be encapsulated (i.e. form a core) in a water-soluble medium. The buffering agent can be part of the core as well, or can remain outside the water-soluble medium. Upon contact with a bodily fluid, the medium encapsulating the sulfonamide compound will slowly dissolve to release the sulfonamide compound, which can then react with malodorous molecules. It is contemplated that the water-soluble medium could be a shell, or a gel, or a liquid, as appropriate for the application.

Generally, the odor-controlling composition containing the sulfonamide compound is applied to an absorbent member by dipping, spraying, or washing. For example, the sulfonamide compound may be mixed with water or another solvent to form an aqueous or other solution, along with the buffering agent. The sulfonamide compound may range from about 0.1% to about 23% (w/v) of the aqueous solution, i.e. about 0.1 to about 23 grams of the sulfonamide compound per milliliter (g/mL) of the aqueous solution. After being applied to the absorbent material, the solvent is allowed to evaporate, leaving behind the active sulfonamide compound. Multiple sprays can be used to increase the amount of active sulfonamide compound on the absorbent member. The active sulfonamide compound can be considered to be impregnated into, or dispersed throughout, or applied onto the absorbent material/absorbent member.

It has been found that due to the stable and hydrated nature of the structure, the sulfonamide compound will activate only when a malodorous molecule is encountered. Minor amounts of water, either through the hydrated active sulfonamide compound and/or the ambient humidity, are sufficient for the sulfonamide to bond with the odor-causing molecules even at ppm and ppb levels.

It has been found that the raw materials that go into making a diaper, such as the absorbent core, absorbent materials, adhesives, non-wovens, poly films, fasteners, elastics, acquisition and distribution layer (ADL), etc., can themselves have a distasteful odor, which can be described as a burnt smell or a smell like rotten grapefruit. It is contemplated that these diaper parts/articles can be impregnated with the odor control composition, so that they do not emit malodorous molecules. Once incorporated into the article, the odor control composition begins to eliminate the odor-causing molecules. Because of the hydrated nature of the odor control composition and the ambient air conditions, there is enough interaction at the ppm and ppb level to effectively control the odors emanating from the otherwise solid materials. Such odors can be removed, eliminated, and/or reduced prior to the diaper parts being combined or manufactured into an absorbent article.

When being used, the active sulfonamide compound present in the absorbent member is activated by coming into contact with bodily fluids (e.g., urine, perspiration, blood). The sulfonamide compound can be chemically activated and then released over time to reduce the odor-causing molecules.

Upon removal of the article from the user, the article now contains much higher levels of fluids due to use. The active sulfonamide compound will continue to react with and reduce the level of malodorous molecules, reducing unwanted odor even further. The active sulfonamide compound continues to actively react with odor-causing molecules over extended periods of time. Even after active use is finished, the odor of treated articles continues to decrease. Treated articles show improved effect over time. Articles worn overnight and for extended time have built-in protection even after extended periods. This is extremely useful for the consumer, as frequent article changes are not necessary until the articles become nearly or completely saturated or due to concentrated urine odors. Further, as the treated products continue to reduce urine odors after removal, disposal of the product is neither evident nor obvious, as the formulation continues to work.

In particular, it is contemplated that the active sulfonamide compound can be used in a diaper or an adult incontinence article. In this regard, urine can contain various sulfur-containing compounds and nitrogen-containing compounds which are particularly pungent when concentrated. In addition, over time, the odor of urine typically gets worse. However, the articles/absorbent members of the present disclosure surprisingly continue to act to reduce such odors. Where it might be expected that the smell of a urinated-in article (e.g. diaper) gets worse over time, such articles that use the sulfonamide compounds of the present disclosure actually have reduced odor. This reduced odor can remain when measured over a period of at least three days (i.e. 72 hours), at least one week (i.e. 168 hours), or even one month (i.e. 720 hours).

The active sulfonamide compounds of the present disclosure are useful in many different productions and many different environments. For example, they can be used on fabrics or hard surfaces in industrial, commercial, and institutional environments such as hospitals. They can also be used in absorbent articles such as diapers, incontinence articles (older children to adults), and pads for various uses such as absorbent pads, feminine pads, pet pads (e.g. for cats to step on when exiting litter box), meat pads (typically included as a liner under meat sold in grocery stores), shoe insoles, gas neutralizing pads, nursing pads, sweat pads (for bras), etc. They can also be used in various wipes such as baby wipes, underarm wipes, body wipes, wet wipes (cleansing pads), moist towelettes, industrial cleaning wipes, pet care wipes, sweat wipes, dish wipes, etc. Wipes differ from absorbent articles as described herein in that wipes are sold moist, while absorbent articles are not (i.e. some of the absorbent capacity of a wipe is already used up). Other articles in which the active sulfonamide compounds could be used could include headbands (to deodorize sweat), furniture (e.g. seat cushions), locker room equipment, filters (for air conditioning, cars, furnaces), etc.

In this regard, a filter includes a substrate having pores therethrough that are sized to block certain materials from passing through the pores while letting others through. The substrate can be made from fibrous materials, and the active sulfonamide compounds are dispersed on the fibers. The fibrous materials may or may not be absorbent. The filter is typically dry, i.e. not moist like a wipe. A fluid stream, typically air, passes through the filter and odorous molecules in the fluid stream react with the active sulfonamide compound on the substrate. The substrate may be of any desired size and shape, and typically is in the form of a pleated paper. A support frame typically surrounds the substrate.

The odor controlling composition containing the active sulfonamide compound may be applied to materials of construction prior to absorbent article construction or during the construction of the absorbent article. Prior to using the odor control composition in the materials for construction, the composition may be used to either remove raw material malodors or pre-treat raw materials so that the odor control composition is on "stand by" when odor molecules are encountered.

Odor molecules may be encountered while the product is still in the bag with other construction materials or when the product is worn (i.e. during use). Raw materials may include any or all materials of construction, such as: a topsheet, acquisition and distribution layer, tissue, core material, super absorbent polymers, a backsheet, stretch laminates, elastics, tab enclosures, adhesives, poly bags (in which another article is enclosed), etc.

Raw materials may not only be pre-treated independently prior to absorbent article construction, but they may also be strategically treated during construction of the product. Varying components may be treated such that there is strategically placed odor control, or multiple components may be treated thereby creating a synergistic effect of all-encompassing odor control.

The odor controlling compositions used to make the odor-controlling articles described herein can be formulated to deliver varying levels of odor control depending on the type of raw material, the location of the raw material in the absorbent article, and the type of desired odor control (e.g., raw material odor, urine odor, bowel movement odor, menses odor, body perspiration odor, pet odors, food/meat odor). The odor controlling composition may further be in the form of a liquid or a solid or any form in between such as a gel or semi-solid, and may be added alone or in conjunction with a solvent. The solvent may be water, alcohol, or another solvent.

The odor-controlling articles of the present disclosure are illustrated by the following non-limiting examples, it being understood that these examples are intended to be illustrative only and that the present application is not intended to be limited to the materials, conditions, process parameters and the like recited herein. All proportions are by weight unless otherwise indicated.

EXAMPLES

Odor was tested and assigned a score of 0 to 10 by an expert panel of humans, with 0 indicating no odor and 10 indicating extreme odor, based on the intensity of the odor. Control articles were generally the articles or substrates that had not been modified with the active formulations. For purposes of this disclosure, the scores are assumed to be linear. For example, an odor that has a score of 7 will be described as having 70% of the odor having a score of 10, an odor with a score of 3 has 30% of the odor having a score of 10, etc. This odor scale applies to all of the examples, so the same score in different examples indicates the same level of odor.

Example 1

Materials and Methods

One set of adult incontinence products (non-fragranced Depends® large female underwear) was treated with approximately sixty (60) pump sprays of 0.5% BENZ active formulation (no fragrance). At 0.13 mL/pump spray, this resulted in a total of 0.039 grams of active compound per absorbent core. For an absorbent core of about 16.8 grams, this results in 0.0023 grams of active sulfonamide compound per gram of absorbent core. A second set of the same products remained untreated as a control. Urine was then collected from 3 different females ranging from 38 to 46 years of age and following different diets intended to yield pungent smelling urine. 20 mL urine was applied to treated and untreated products simultaneously. This resulted in about 1.95 mg active compound per mL of urine. Note the urine was applied to the center of the product, simulating where urine is typically discharged. Thus, the urine was not evenly distributed across the entire surface of the absorbent core, and the efficacy of the active compound is even greater than indicated below. The products were evaluated on odor at time of application and at 1, 3, and 7 minutes after application. Each product was then placed in a plastic bag and sealed before being evaluated for odor after an extended time period (1440 minutes).

Results

Figure 2A:
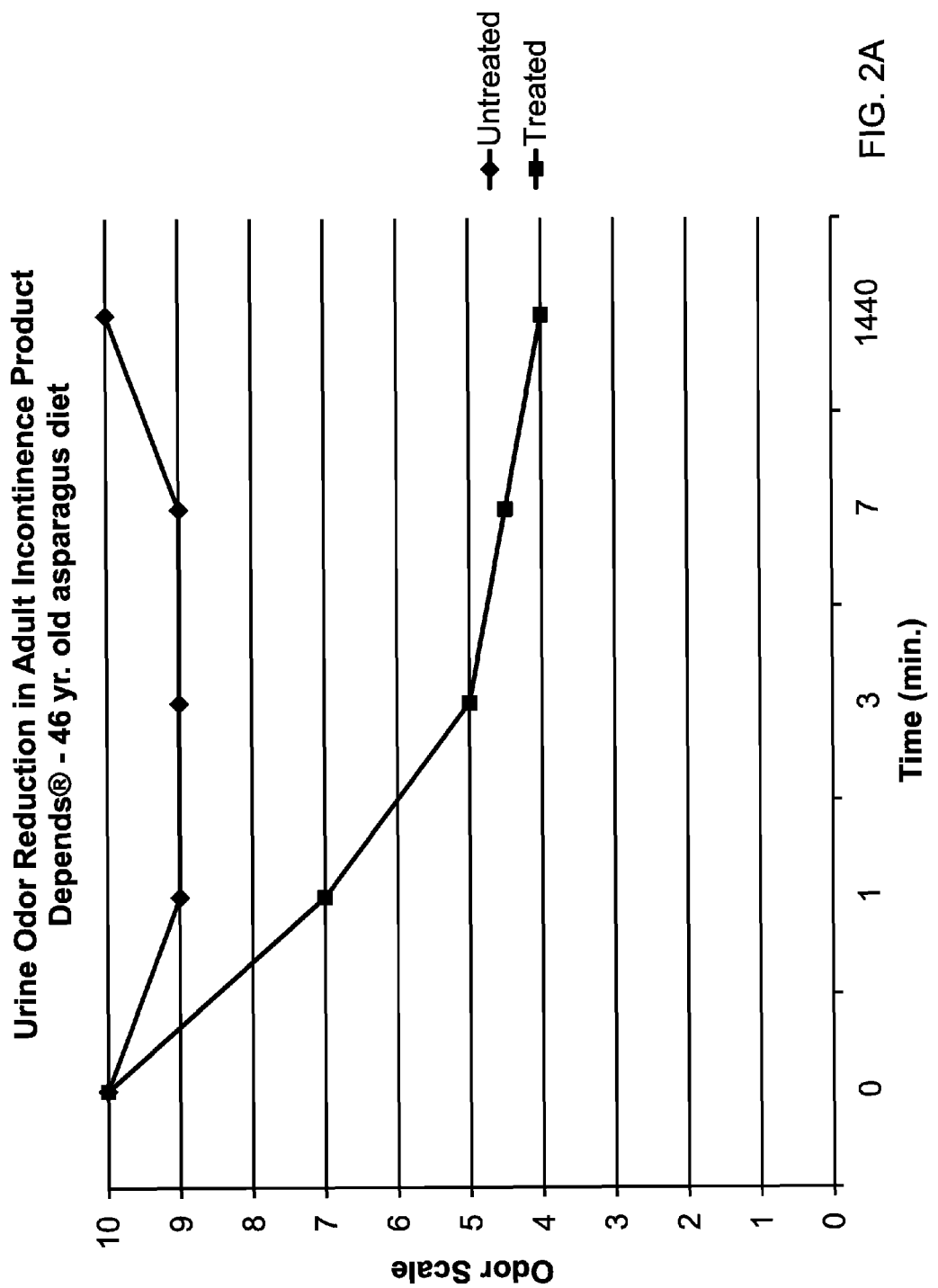
FIGS. 2A-2C are a set of graphs comparing the urine odor reduction over 24 hours between an untreated and a treated Depends® adult incontinence products from three individuals.
Figure 2B:
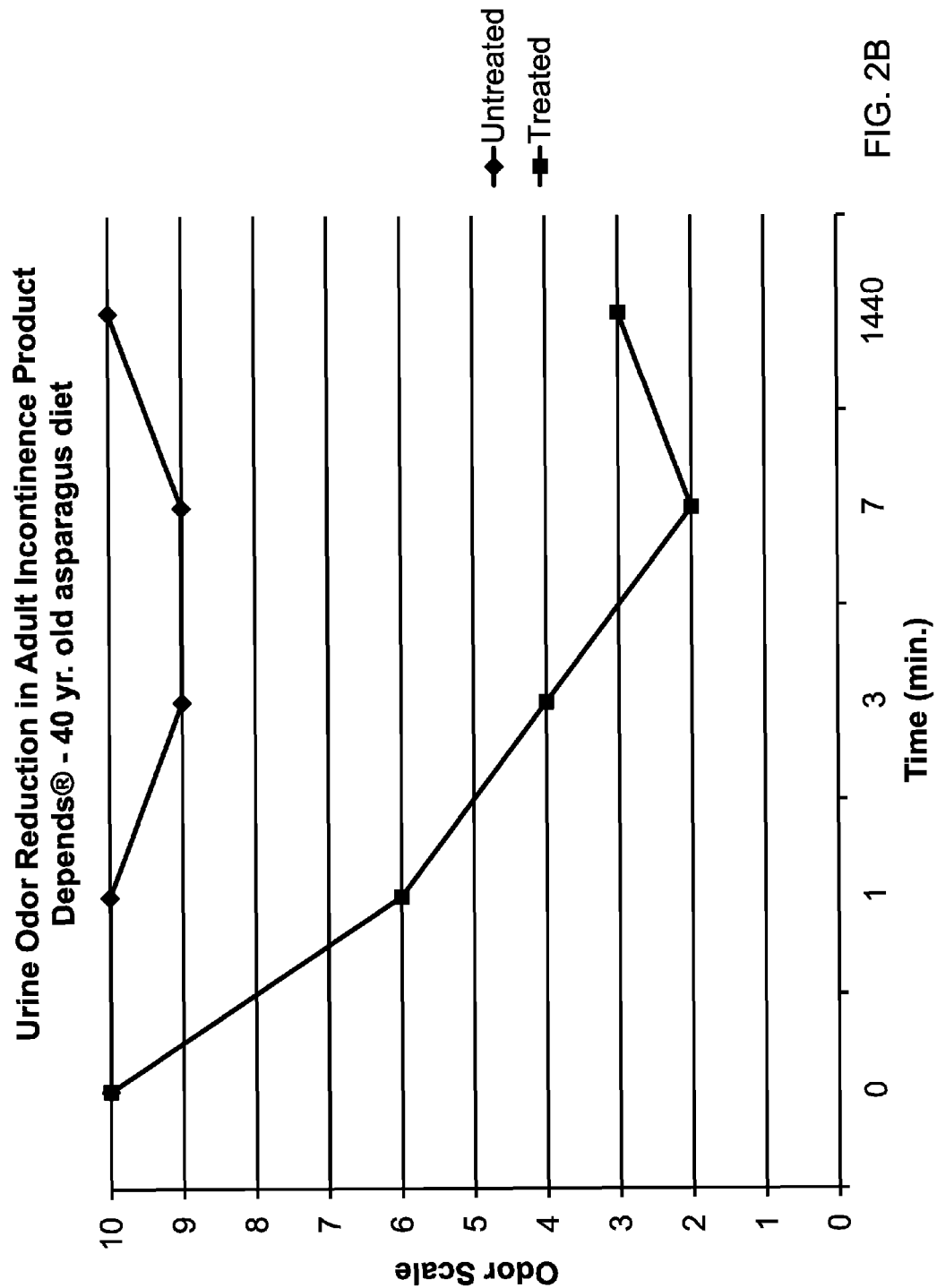
Figure 2C:
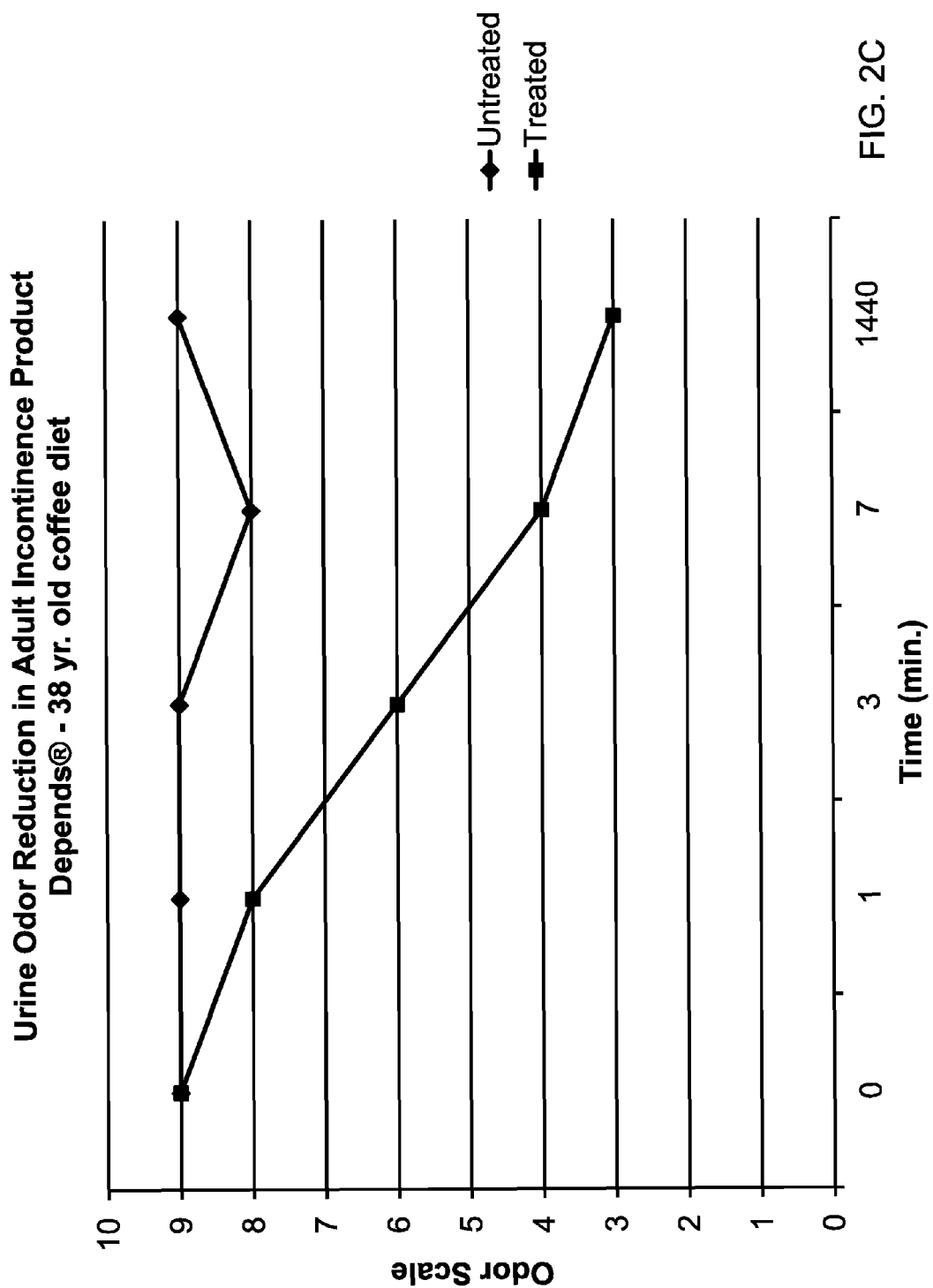

As shown in the odor scale scores of Table 2 below and FIGS. 2A-2C, treated products exhibited a reduction in odor after as little as 1 minute after application of urine, while untreated products retained a strong odor with an odor score of at least 8.

TABLE 2

| Time (min.) | 46 yr. old female (concentrated asparagus diet) | | 40 yr. old female (concentrated asparagus diet) | | 38 yr. old female (concentrated coffee diet) | |
|---|---|---|---|---|---|---|
| | Untreated | Treated | Untreated | Treated | Untreated | Treated |
| 0 | 10 | 10 | 10 | 10 | 9 | 9 |
| 1 | 9 | 7 | 10 | 6 | 9 | 8 |
| 3 | 9 | 5 | 9 | 4 | 9 | 6 |
| 7 | 9 | 4.5 | 9 | 2 | 8 | 4 |
| 1440 | 10 | 4 | 10 | 3 | 9 | 3 |

Across all three treated samples, urine malodor was reduced to below 50% of the original odor within 7 minutes. At 24 hours (i.e. 1440 minutes), the urine malodor was 40% or less of the original odor and the untreated odor in all treated samples.

Example 2

Materials and Methods

One adult incontinence product (non-fragranced Depends® large female underwear) was treated with approximately sixty (60) pump sprays of 0.5% BENZ active formulation (no fragrance) (0.039 grams of active compound per absorbent core). For an absorbent core of about 16.8 grams, this results in 0.0023 grams of active sulfonamide compound per grams of absorbent core. A second of the same product remained untreated as a control. Urine was then collected from one 71-year old female during the day and overnight. 50 mL of each type of urine was applied to treated and untreated products simultaneously. This resulted in about 0.78 mg active compound per mL of urine. Note the urine was applied to the center of the product, simulating where urine is typically discharged. Thus, the urine was not evenly distributed across the entire surface of the absorbent core. The products were evaluated on odor at the time of application and at 1, 3, and 7 minutes after application. Each product was then placed in a plastic bag and sealed before being evaluated for odor after an extended time period (1440 minutes).

Results

Figure 3:
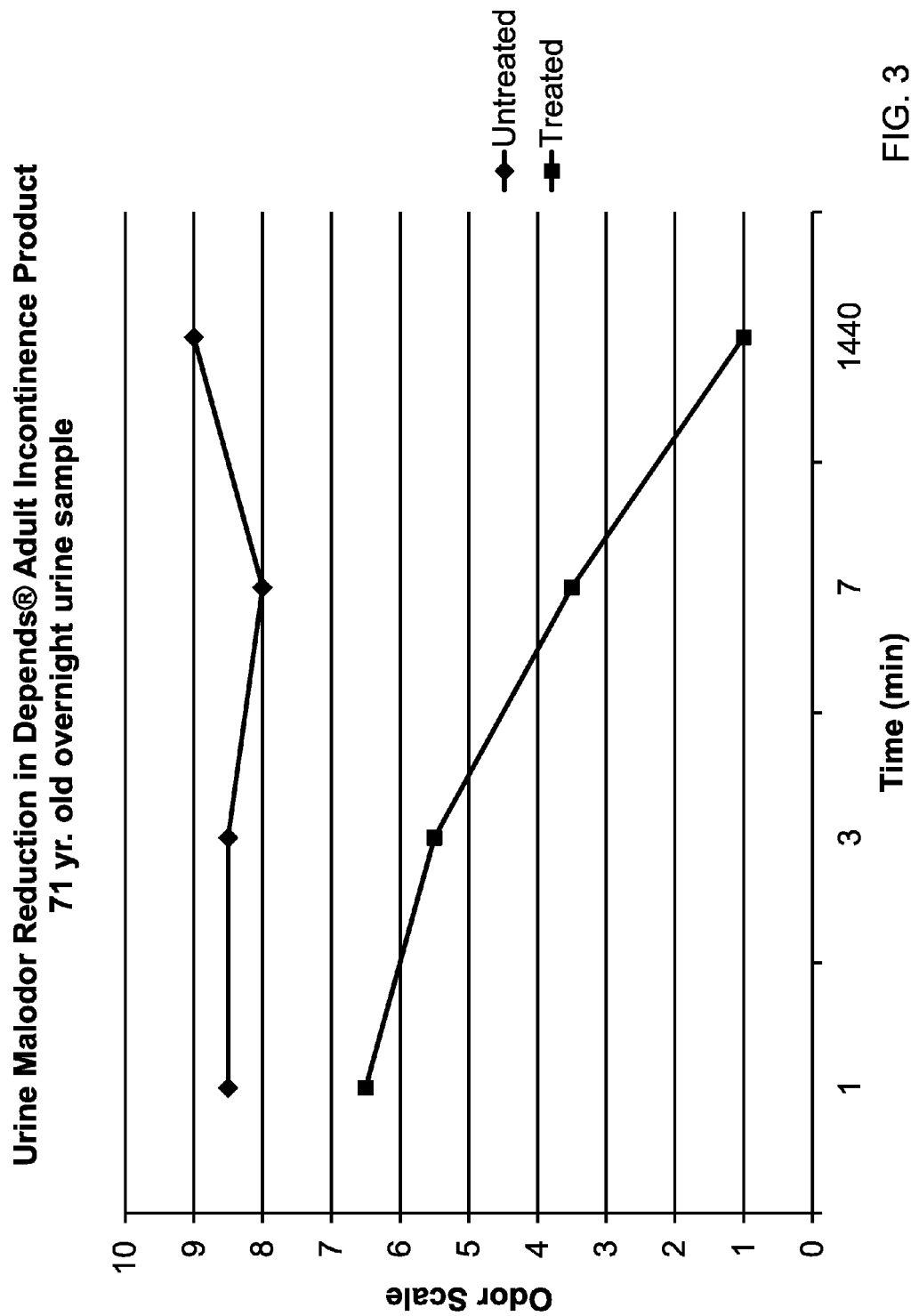
FIG. 3 is a graph comparing the urine odor reduction over 24 hours between an untreated and a treated Depends® adult incontinence product from a 71-year old female. Odor was evaluated on a scale from 0 to 10 (y-axis), with 10 representing strong odor.

As shown in the odor scale scores of Table 3 below and FIG. 3, treated products exhibited a reduction in odor after as little as 1 minute after application of urine, while untreated products retained a strong odor with an odor score of at least 8.

TABLE 3

| Time (min.) | Day | | Overnight | |
|---|---|---|---|---|
| | Untreated | Treated | Untreated | Treated |
| 0 | 8 | 8 | | |
| 1 | 8 | 7 | 8.5 | 6.5 |
| 3 | 8 | 7 | 8.5 | 5.5 |
| 7 | 8 | 6 | 8 | 3.5 |
| 1440 | 9 | 2 | 9 | 1 |

Across all treated samples, urine malodor was reduced by at least 25% within 7 minutes. At 24 hours (i.e. 1440 minutes), urine malodor was still reduced by at least 75% in all treated samples.

Example 3

Materials and Methods

One adult incontinence product (Always Discreet Pad Ultimate Absorbency Long Length-Fragranced Always) was treated with approximately sixty (60) pump sprays of 0.75% BENZ active formulation (no fragrance) (i.e. 0585 grams active compound per absorbent core). A second of the same product was left untreated as a control. Urine was then collected from one 46-year old female. 60 mL urine was applied to treated and untreated products simultaneously. Later, an additional 40 mL urine was simultaneously applied to treated and untreated products. Products were evaluated on odor at time of application and 3 hours after application. This resulted in about 0.585 mg active compound per mL of urine. Again, the urine was applied to the center of the product, simulating where urine is typically discharged, and was not evenly distributed across the entire surface of the absorbent core.

Results

Figure 4:
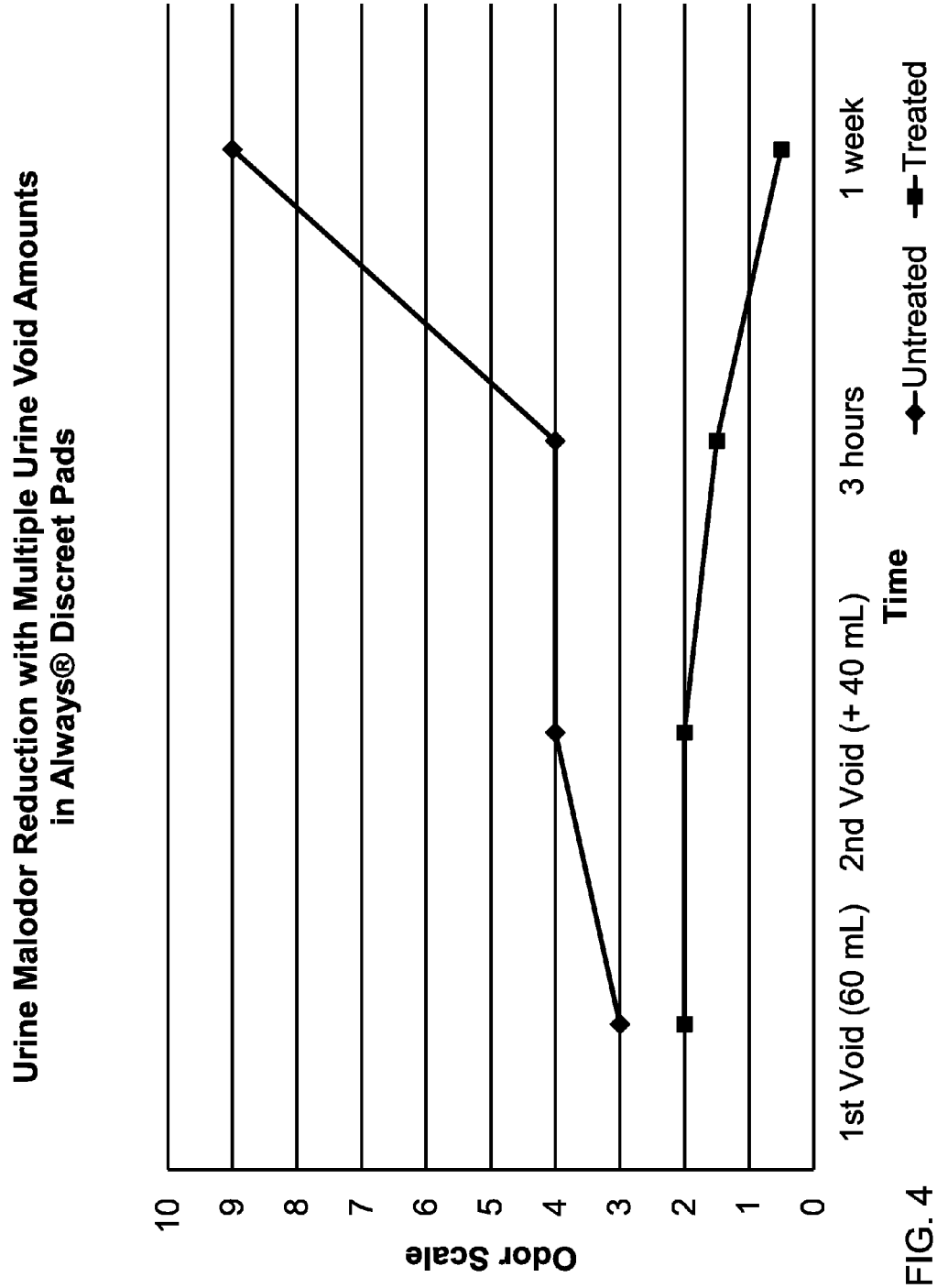
FIG. 4 is a graph comparing urine odor reduction after multiple voids between an untreated and a treated Always® Discreet adult incontinence product. Odor was evaluated on a scale from 0 to 10 (y-axis), with 10 representing strong odor.

As shown in the odor scale scores of Table 4 below and FIG. 4, treated products exhibited a reduction in odor upon application of urine, while untreated products retained a strong odor.

TABLE 4

| | Untreated | Treated |
|---|---|---|
| 60 mL of urine | | |
| Overall fragrance intensity | 8 | 4.5 |
| Overall urine | 3 | 2 |
| Additional 40 mL urine (total 100 mL) | | |
| Overall fragrance intensity | 7.5 | 4 |
| Overall urine | 4 | 2 |
| 3 hours later | | |
| Overall fragrance intensity | 5 | 3 |
| Overall urine | 4 | 1.5 |
| 1 week later | | |
| Overall fragrance intensity | | |
| Overall urine | 9 | 0.5 |

Urine malodor and overall fragrance intensity was reduced by over 80% over the course of three hours. After one week, the overall urine odor was still less than 10% of both the untreated odor.

Example 4

Materials and Methods

One adult incontinence product (topsheet of Always Discreet Underwear S/M Maximum Absorbency) was treated with approximately 75 pump sprays of 0.75% BENZ active formulation (no fragrance) (0.073 grams active compound). A second of the same product (topsheet) was treated with approximately 120 pump sprays of 1% BENZ active formulation (no fragrance) (0.156 grams active compound). A third product remained untreated as a control. Dry weight of the product alone was 54.8 grams with a core weight of approximately 19.2 grams. One 46-year old female voided overnight into each sample product. Each product was removed for odor evaluation at time of urine application and then at 1 hour, 3 hours, and 6 hours after application. Each product was then placed in a plastic bag and sealed for an extended period before odor evaluation at 1 week. Because the products were used, the amount of liquid voided varied between the products.

Results

Figure 5:
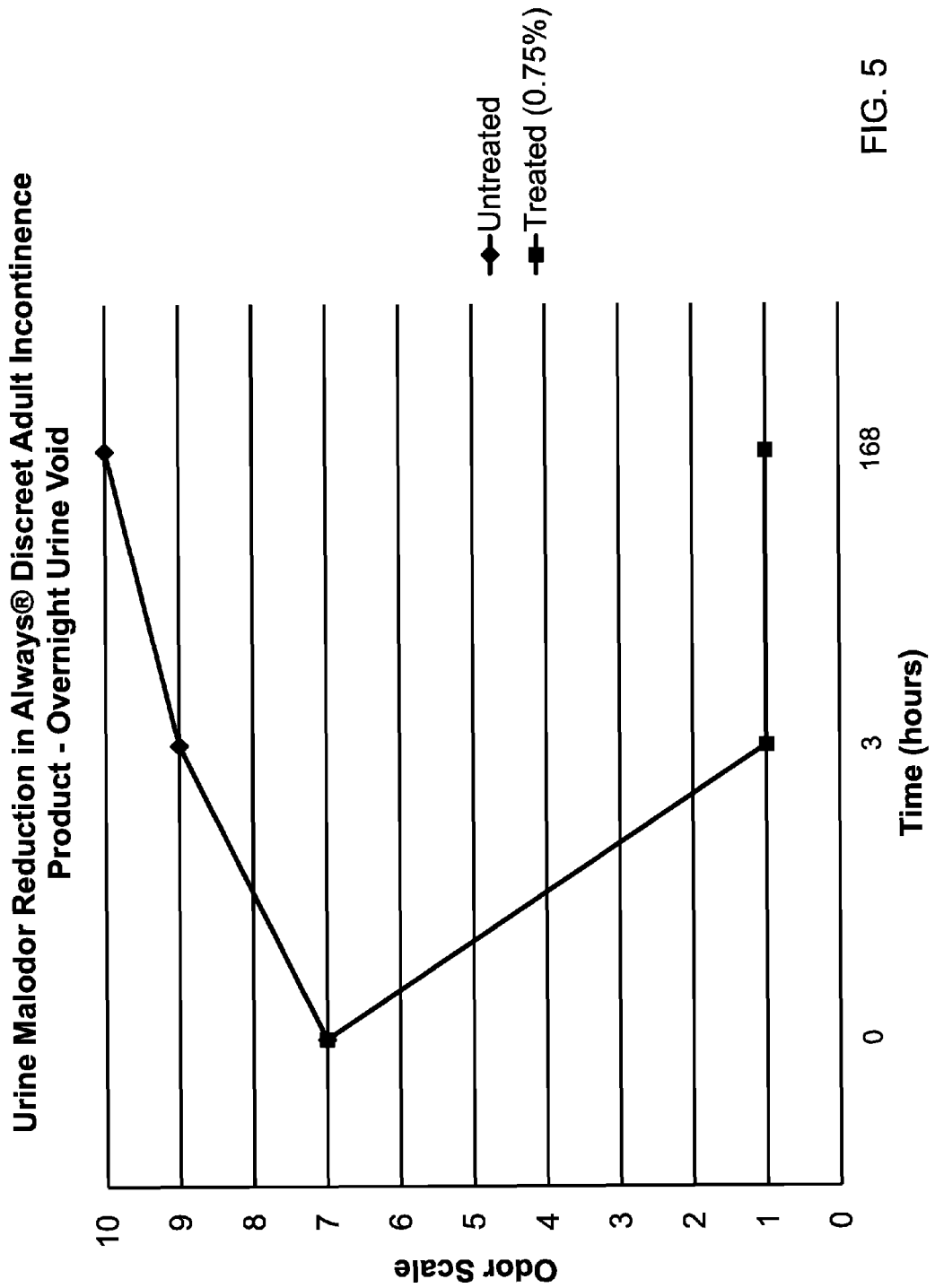
FIG. 5 is a graph comparing urine odor reduction after overnight void between an untreated and a treated Always®

As shown in the odor scale scores of Table 5 below and FIG. 5, treated products exhibited a significant reduction in odor within 3 to 6 hours of use, and treated products continued to demonstrate less urine malodor as time increased. However untreated products exhibited an increase in urine malodor over time. At one week, the treated odors were roughly 15% of the untreated odor.

TABLE 5

| Time (hrs) | Untreated Wet Wt. = 643.3 grams | Treated Topsheet (0.75% Active) Wet Wt. = 434.3 grams | Treated Topsheet (1% Active) Wet Wt. = 517.2 grams |
|---|---|---|---|
| 0 | 7 | 7 | 5 |
| 1 | | | 6 |
| 3 | 9 | 1 | |
| 6 | | | 1 |
| 168 (1 week) | 10 | 1 | |

Example 5

Materials and Methods

One adult incontinence product (core of Depends® large female underwear) was treated with approximately 80 pump sprays of 1% BENZ active formulation (no fragrance) (0.104 grams active compound) onto the absorbent core. A second of the same product (core) was treated with approximately 120 pump sprays of 1% BENZ active formulation (no fragrance) (0.156 grams active compound). Dry weight of the product alone was 44.7 grams with a core weight of approximately 16.8 grams. One 46-year old female voided twice into each sample product. Each product was removed for odor evaluation after two hours and then placed in a plastic bag and sealed for an extended period before odor evaluation at 3 days.

Results

As shown in the odor scale scores of Table 6 below, the treated products exhibited a significant reduction in odor over time even when leakage occurred. After 3 days, the odor remains reduced below 70% of the original odor in both treated products.

TABLE 6

| | Treated Core (80 pumps of 1% active) Wt. = 277 grams | Treated Core (120 pumps of 1% active) Wt. = 427 grams |
|---|---|---|
| 1st Void | 6 | 8 |
| 2nd Void at 1 hr | 8 (leakage) | Overnight urine |
| 2 hrs | 7.5 (leakage) | |
| 72 hrs (3 days) | 4 | 5 |

Example 6

Materials and Methods

Two Pampers Cruisers (size 4) fragranced baby products were treated with approximately 60 pump sprays of 1% BENZ active formulation (no fragrance) (0.078 grams active compound) each. A third of the same product was left untreated as a control. Dry weight of the product alone was 37.6 grams with a core weight of approximately 6.1 grams. In turn, each product was applied to a baby and worn overnight. In the morning, each product was removed and the urine malodor observed over time.

Results

As shown in the odor scale scores of Table 7 below, the treated products exhibited a significant reduction in odor over time. However, the untreated product malodor increased over time.

TABLE 7

| Time After Diaper Removed (hrs.) | Untreated Core (worn ~12.25 hrs.) Wet Wt. = 269.9 grams | Treated Core (worn ~11.25 hrs.) Wet Wt. = 252.5 grams | Treated Core (worn ~12 hrs.) Wet Wt. = 276.6 grams |
|---|---|---|---|
| 0 | 6 | | |
| 1.5 | | 1.5 | |
| 3 | | | 2 |
| 24 | 8 | | |

Example 7

Materials and Methods

Two Huggies Overnights (size 4) baby products were treated with approximately 60 pump sprays of 0.75% BENZ active formulation (no fragrance) (0.0585 grams active compound) each. Four products of the same were left untreated as controls. Dry weight of the product alone was 45.2 grams with a core weight of approximately 23.9 grams. In turn, each product was applied to a baby and worn overnight. In the morning, each product was removed and the urine malodor observed over time.

Results

As shown in the odor scale scores of Table 8 below, the treated products exhibited a reduction in odor compared to the untreated products. The products with an asterisk in Table 8 indicate the child was teething and running a fever.

TABLE 8

| Untreated (worn ~12 hrs.) Wet Wt. = 374.4 grams | Untreated* (worn ~12 hrs.) Wet Wt. = 333.9 grams | Untreated (worn ~13.5 hrs.) Wet Wt. = 227.5 grams | Untreated (worn ~11.25 hrs.) Wet Wt. = 361.2 grams | Treated* (worn ~12.75 hrs.) Wet Wt. = 360.4 grams | Treated* (worn ~10 hrs.) Wet Wt. = 286.3 grams |
|---|---|---|---|---|---|
| 10 | 10 | 9 | 9 | 8.5 | 8.5 |

Example 8

Materials and Methods

Topsheets of size 4 baby products were treated with approximately 30 pump sprays of 0.5% BENZ active formulation (no fragrance) (0.0195 grams active compound per gram of absorbent material) each. A set of the same products were left untreated as controls. Treated products were placed together in a bag, while untreated products were placed together in a separate bag. The products were kept in the sealed bags for about one month. Next, overnight urine was acquired from a 46-year old female in the morning. The urine was then kept at room temperature for 4 hours before each product was treated with 100 mL of urine. This resulted in about 0.195 mg active compound per mL of urine. Again, the urine was applied to the center of the product, simulating where urine is typically discharged, and was not evenly distributed across the entire surface of the absorbent core, to the efficacy of the active compound is greater than indicated.

Results

As shown in the odor scale scores of Table 9 below, the treated products exhibited a reduction in odor compared to the untreated products. After 12 hours, significant urine malodor reduction was observed in the treated products—they were all about 40% of their original odor, and about 40% lower compared to the untreated odor.

TABLE 9

| Time-product exposed to air (min.) | Pampers® Baby Dry | | Pampers® Swaddlers | | Luvs® | | Huggies® | |
|---|---|---|---|---|---|---|---|---|
| | Untreat | Treat | Untreat | Treat | Untreat | Treat | Untreat | Treat |
| 0 | 8 | 8 | 8 | 8 | 9 | 9 | 9 | 9 |
| 0.5 | 8 | 8 | 8 | 8 | 9 | 9 | 9 | 9 |
| 1 | 8 | 7 | 7 | 7 | 9 | 8 | 9 | 8 |
| 5 | 8 | 6 | 7 | 7 | 8 | 6 | 7 | 5 |
| 10 | 7 | 5 | 6 | 6 | 7 | 5 | 7 | 4 |
| 30 | 7 | 5 | 5 | 5 | 6 | 5 | 6 | 4 |
| 60 | 5 | 4 | 3 | 3 | 4 | 4 | 4 | 2 |
| 720 | 7 | 3 | 7 | 2 | 7 | 4 | 7 | <2 |

Example 9

Materials and Methods

The active formulation was made using 1% BENZ and 0.5% sodium bicarbonate. 120 sprays (0.156 grams active compound) was then added to two different products: (1) Depends® for Women Underwear with Fit-Flex Protection Moderate Absorbency S/M (28-40 in"/71-102 cm waist); and (2) Always® Discreet. A set of the same products was put aside to serve as controls, and 150 mL urine (asparagus diet and overnight first morning void) was administered to each product. This resulted in approximately 1.04 milligrams of active compound per mL of urine. Again, the urine was applied to the center of the product, simulating where urine is typically discharged, and was not evenly distributed across the entire surface of the absorbent core, so the efficacy of the active compound is greater than indicated.

Results

As shown in the odor scale scores of Table 10 below, the treated products exhibited a significant reduction in odor compared to the untreated control products. After 24 hours, the treated products were 40% or less of the original odor.

TABLE 10

| | Depends® | | Always® | |
|---|---|---|---|---|
| Time | Control | Treated | Control | Treated |
| <30 sec. | 7 | 5 | 7 | 6 |
| 1 min. | 8 | 8 | 6.5-7 | 3 |
| 3 min. | 7 | 3.5 | 6.5-7 | 3 |
| 7 min. | 6.5-7 | 3 | 6.5 | 2-2.5 |
| 10 min. | 6.5 | 2-2.5 | 6-6.5 | 1 |
| 30 min. | 6-6.5 | 1.5-2 | 6 | 0-0.5 |
| 24 hours | 6-6.5 | 2 | 6.5-7 | 0.5 |

Example 10

Materials and Methods

To evaluate the efficacies of different active formulations on urine malodor reduction as well as evaluate the threshold for active formulation levels over time with multiple voids, two different active formulations were prepared. FB05 consisted of 5% BENZ and 0.75% sodium bicarbonate. FT05 was prepared from 5% Chloramine-T and 0.75% sodium bicarbonate. 24 sprays of FB05 (0.156 grams active compound) was then added to one Depends® for Women Underwear with Fit-Flex Protection Moderate Absorbency S/M (28-40"/71-102 cm), and 24 sprays of FT05 (0.156 grams active compound) was added to a second identical product. The topsheet of the product was peeled back, exposing the absorbent core material. The active formulation was sprayed onto the absorbent core material and allowed to air dry. The top sheet was then placed back onto the core material. A third of the same product was put aside to serve as the control.

Next, 150 mL urine was administered to each product. The administered urine was a combined specimen of overnight urine and urine taken from subjects observing an asparagus diet, a caffeine diet. Odor was scored periodically.

Two hours after the first urine application, 75 mL of the combined urine was added to each product, bringing the total urine volume to 225 mL per product. After another hour, an additional 75 mL combined urine was added to each product, bringing the total urine volume to 300 mL per product. This resulted in approximately 0.52 milligrams of active compound per mL of urine. Again, the urine was applied to the center of the product, simulating where urine is typically discharged, and was not evenly distributed across the entire surface of the absorbent core, so the efficacy of the active compound is greater than indicated.

Results

As shown in the odor scale scores of Table 11 below, the treated products with both active formulations exhibited a significant reduction in odor compared to the untreated control products. After 24 hours, the odor of the treated products remained very low, about 15% of their original odor and of the untreated odor. As expected, over 3 days the odor increased, but the treated products still performed better than the control. At 7 days, due to the larger void volume of 300 ml for a moderate absorbent product and the urine location being about one third of the treated core area, the urine odor increased on all products.

TABLE 11

| Time | Control | FB05 | FT05 |
|---|---|---|---|
| 0-5 min. | 7-8 | 1-1.5 | 3 |
| 10 min. | 7-8 | 1.5 | 2 |

TABLE 11-continued

| Time | Control | FB05 | FT05 |
|---|---|---|---|
| 30 min. | 7-8 | 1.5-2 | 2 |
| 45 min. | 6-7 | 1-1.5 | 2 |
| 1 hour | 6-7 | 1 | 1.5 |
| 2 hours | 5-6 | 1 | 1 |
| Additional 75 mL urine (total 225 mL urine) | | | |
| 2 hours | 6-7 | 3 | 3 |
| 3 hours | 5 | 1 | 1 |
| Additional 75 mL urine (total 300 mL urine) | | | |
| 3.5 hours | 6-7 | 1 | 1 |
| 4 hours | 6 | 1 | 1 |
| 6 hours | 6 | 1 | 1 |
| 24 hours | 6.5-7 | 1 | 1 |
| 3 days | 7-7.5 | 3-3.5 | 2-3 |
| 7 days | 8-9 | 8-9 | 8-9 |

Example 11

Materials and Methods

To evaluate the efficacies of different active formulations on urine malodor reduction as well as evaluate the threshold for active formulation levels over time with multiple voids, two different active formulations were prepared. FB20 consisted of 20% BENZ and 1% sodium bicarbonate. FT10 was prepared from 10% Chloramine-T and 1.3% sodium bicarbonate. FB20FT1020 sprays of FB20 (0.52 grams active compound) was then added to one Tranquility Premium Protection Maximum Protection 1005 mL SmartCore Daytime/Nighttime Disposable Briefs-Size L, and 40 sprays of FT10 (0.52 grams active compound) was added to a second identical product. The topsheet of the product was peeled back, exposing the absorbent core material. The active formulation was sprayed onto the absorbent core material and allowed to air dry. The top sheet was then placed back onto the core material. A third of the same product was put aside to serve as the control, and 200 mL urine was administered to each product. The administered urine was a combined specimen of overnight urine and urine taken from subjects observing an asparagus diet, a caffeine diet. Odor was scored periodically.

Forty-five minutes after urine application, 200 mL combined urine was added to each product, bringing the total urine volume to 400 mL per product. After another 1.25 hours, an additional 200 mL combined urine was added to each product, bringing the total urine volume to 600 mL per product. This resulted in approximately 0.87 milligrams of active compound per mL of urine. Again, the urine was applied to the center of the product, simulating where urine is typically discharged, and was not evenly distributed across the entire surface of the absorbent core, so the efficacy of the active compound is greater than indicated.

Results

As shown in the odor scale scores of Table 12 below, the treated products with both active formulations exhibited a significant reduction in odor compared to the untreated control products. The treated products still had very weak odor after 3 days, and were still 50% of the odor of the control product.

TABLE 12

| Time | Control | FB20 | FT10 |
|---|---|---|---|
| 0-5 min. | 7-8 | 1-2 | 1-2 |
| 10 min. | 7-8 | 1-2 | 1-2 |
| 30 min. | 7-8 | 1-2 | 1-2 |
| Additional 200 mL urine (total 400 mL urine) | | | |
| 45 min. | 7-8 | 2 | 2 |
| 1 hour | 6-7 | 1.5-2 | 1.5-2 |
| 2 hours | 6-7 | 1-1.5 | 1-1.5 |
| Additional 200 mL urine (total 600 mL urine) | | | |
| 2 hours | 7-8 | 3 | 3 |
| 3 hours | 7 | 1-1.5 | 1-1.5 |
| 4 hours | 6-7 | 1-1.5 | 1-1.5 |
| 6 hours | 6 | 1.5 | 1 |
| 8 hours | 6 | 1.5 | 1 |
| 12 hours | 5 | 0.5-1 | 0.5-1 |
| 24 hours | 6-7 | <1 | <1 |
| 3 days | 7 | <1 | <1 |
| 1 week | 8 | 3-4 | 3-4 |

Example 12

Materials and Methods

To evaluate the efficacy of an active formulation on urine malodor reduction when applied to a topsheet compared to core material as well as evaluate the threshold for an active formulation level over time with multiple voids, one active formulation was prepared. FB20 consisted of 20% BENZ and 1% sodium bicarbonate. FB2020 sprays of FB20 (0.52 grams active compound) was then added to the topsheet of one Tranquility Premium Protection Maximum Protection 1005 mL SmartCore Daytime/Nighttime Disposable Briefs-Size L. 20 sprays of FB20 (0.52 grams active compound) was added to the core of a second identical product. The topsheet of the product was peeled back, exposing the absorbent core material. The active formulation was sprayed onto the absorbent core material and allowed to air dry. The top sheet was then placed back onto the core material. A third of the same product was set aside to serve as the control, and 300 mL urine was administered to each product. The administered urine was a combined specimen of overnight urine and urine taken from subjects observing an asparagus diet, a caffeine diet. Odor was scored periodically.

Ten minutes after urine application, 300 mL combined urine was added to each product, bringing the total urine volume to 600 mL per product. This resulted in approximately 0.87 milligrams of active compound per mL of urine. Again, the urine was applied to the center of the product, simulating where urine is typically discharged, and was not evenly distributed across the entire surface of the absorbent core, so the efficacy of the active compound is greater than indicated.

Results

As shown in the odor scale scores of Table 13 below, the treated products with the active formulation exhibited a significant reduction in odor compared to the untreated control product. The odor reduction was approximately the same in both the topsheet and the core, and both were about 25% of the odor of the untreated control.

TABLE 13

| Time | Control | Topsheet | Core |
|---|---|---|---|
| 1 min. | 7-8 | 3 | 3 |
| 5 min. | 7 | 2 | 2 |
| 10 min. | 7 | 2 | 2 |

TABLE 13-continued

| Time | Control | Topsheet | Core |
|---|---|---|---|
| Additional 300 mL urine (total 600 mL urine) | | | |
| 10 min. | 8 | 3 | 4 |
| 30 min. | 7 | 2 | 3 |
| 1 hour | 6.5-7 | 2 | 3 |
| 2 hours | 6-7 | 2 | 3 |
| 3 hours | 6.5 | 2-2.5 | 2 |
| 4 hours | 6-6.5 | 2 | 2 |
| 6 hours | 7 | 1 | 2 |
| 8 hours | 7.5-8 | 1 | 2 |
| 12 hours | 8 | 1.5-2 | 2-2.5 |
| 24 hours | 8 | 2 | 2 |

Example 13

Materials and Methods

To evaluate the efficacy of an active formulation at a lower application on urine malodor reduction as well as evaluate the threshold for an active formulation level over time with multiple voids, one active formulation was prepared. FB20 consisted of 20% BENZ and 1% sodium bicarbonate. 11 sprays of FB20 (0.286 grams active compound) was then added to the core of one Tranquility Premium Protection Maximum Protection 1005 mL SmartCore Daytime/Nighttime Disposable Briefs-Size L. A second of the same product was set aside to serve as the control.

300 mL urine was administered to each product. The administered urine was a combined specimen of overnight urine and urine taken from subjects observing an asparagus diet, a caffeine diet. Odor was scored periodically. Ten minutes after urine application, 300 mL combined urine was added to each product, bringing the total urine volume to 600 mL per product. This resulted in approximately 0.48 milligrams of active compound per mL of urine. Again, the urine was applied to the center of the product, simulating where urine is typically discharged, and was not evenly distributed across the entire surface of the absorbent core, so the efficacy of the active compound is greater than indicated.

Results

As shown in the odor scale scores of Table 14 below, the treated product with the active formulation exhibited a significant reduction (approximately 50%) in odor compared to the untreated control product.

TABLE 14

| Time | Control | Treated Core |
|---|---|---|
| 1-5 min. | 7 | 2-3 |
| 10 min. | 7 | 2 |
| Additional 300 mL urine (total 600 mL urine) | | |
| 10 min. | 8 | 3-4 |
| 45 min. | 7 | 3-4 |
| 1 hour | 6-7 | 4 |
| 2 hours | 6-7 | 3-4 |
| 3 hours | 6.5-7 | 3-3.5 |
| 4 hours | 6.5-7 | 3.5 |
| 6 hours | 7.5 | 3 |
| 8 hours | 7.5-8 | 3 |
| 12 hours | 7.5-8 | 3.5-4 |
| 24 hours | 7.5-8 | 3-4 |

Example 14

Materials and Methods

5% BENZ and sodium bicarbonate was used to create an active formulation. 70 sprays of the active formulation (0.0455 grams of active compound) was then applied to 5 grams super absorbent polymer (SAP) raw material, which was expected to absorb any liquid formulation. This was approximately 0.009 grams of active compound per gram of SAP. Urine specimens for testing included fox and mink urine.

Results

As shown in the odor scale scores of Table 15 below, the treated SAP exhibited a significant reduction in odor compared to the untreated controls. Each drop was about 0.02 grams in weight.

TABLE 15

| | Fox Urine (6 drops) | | Mink Urine (3 drops) | |
|---|---|---|---|---|
| Time | Treated | Control | Treated | Control |
| 3-5 min. | 3-4 | 6-7 | 5-6 | 6-7 |
| 15 min. | 0 (urine odor); 2 (chlorine odor) | 3-4 | 3 | 6 |

Example 15

Materials and Methods 0.4 grams dry Chloramine-T was applied to 3 grams super absorbent polymer (SAP) (~11.7 wt % active compound, 0.13 grams active compound per gram of SAP). Undiluted mink urine was used for testing. Each drop was about 0.02 grams in weight.

Results

As shown in the odor scale scores of Table 16 below, 11.7% active formulation pre-treated SAP exhibited an immediate elimination of malodors.

TABLE 16

| Time (min.) | Mink Urine (4 drops) |
|---|---|
| 0 | 0 (no mink malodor) |
| 1 | 0 (no mink malodor) |

Example 16

Materials and Methods 0.3 grams dry Chloramine-T was applied to 5.99 grams super absorbent polymer (SAP) (~4.8 wt % active compound, 0.05 grams active compound per gram of SAP). Undiluted fox urine was used for testing.

Three drops of undiluted fox urine was initially applied to SAP. Approximately every 1-2 minutes thereafter, 3-11 more drops undiluted fox urine were applied to the SAP for an eventual total of about 40 drops per sample. Each drop was about 0.02 grams in weight Results As shown in the odor scale scores of Table 17 below, 4.8% active formulation pre-treated SAP (with no buffer) exhibited an immediate urine malodor reduction. As more urine was added to the treated SAP, the malodor remained at least 50% lower compared to the control.

TABLE 17

| Time | Control | Treated SAP |
|---|---|---|
| 0 min. | 7 | 2 |
|  |  | <2 (chlorine odor) |
| 1 min. | 7 | 1-2 |
|  |  | 1-2 (amine odor) |
| >2 min. | 7 | <1 |
|  |  | 0-2 (chlorine odor) |
|  |  | 1-2 (amine odor) |
| Additional 3 drops urine (total 6 drops urine) | | |
| 0 min. | 7-8 | 2-5 |
|  |  | 1 (chlorine odor) |
|  |  | 0 (amide odor) |
| >1 min. | 6-7 | <2 |
|  |  | <1 (chlorine odor) |
|  |  | 1-2 (amide odor) |
| Additional 3 drops urine (total 9 drops urine) | | |
| 0 min. | 8 | 2 |
| >1 min. | 6-7 | 1-2 |
|  |  | 0 (chlorine odor) |
|  |  | 1-2 (amine odor) |
| Additional 3 drops urine (total 12 drops urine) | | |
| 0 min. | 8-9 | 3-5 |
| >1 min. | 8-9 | <3 |
|  |  | 1-2 (chlorine odor) |
| >2 min. | 7-8 | <3 |
|  |  | <1 (chlorine odor) |
|  |  | 1-2 (other odor) |
| Additional 3 drops urine (total 15 drops urine) | | |
| 0 min. |  |  |
| >1 min. | 8+ | 3 |
|  |  | <1 (chlorine odor) |
|  |  | 1-2 (amide odor) |
| >2 min. | 8+ | 3 |
|  |  | 0 (chlorine odor) |
|  |  | 1-2 (amide odor) |
| Additional 5 drops urine (total 20 drops urine) | | |
| 0 min. |  |  |
| >1 min. | 8 | 3-4 |
| >2 min. | 8 | 2-3 |
|  |  | 1 (chlorine odor) |
|  |  | 2 (other odor) |
| Additional 11 drops urine (total 31 drops urine) | | |
| 0 min. |  |  |
| >1 min. | 8+ | 2-3 |
|  | 5-6 (ammonia odor) | 3 (ammonia odor) |
| >2 min. | 8 | 1 |
|  | <5 (ammonia odor) | 0 (chlorine odor) |
|  |  | 1 (amine odor) |
|  |  | 2 (ammonia odor) |
| Additional 9 drops urine (total 40 drops urine) | | |
| 0 min. |  |  |
| >1 min. | 8-9 | <1 |
|  | 5-6 (ammonia odor) | 5 (ammonia odor) |
| >2 min. | 8-9 | <1 |
|  | 5-6 (ammonia odor) | 0 (chlorine odor) |
|  |  | 0 (amide odor) |
|  |  | 5-6 (ammonia odor) |

Example 17

Materials and Methods 0.3 grams dry Chloramine-T was applied to 6 grams super absorbent polymer (SAP) (~4.8 wt % active compound, 0.05 grams active compound per gram of SAP) for a first sample with no buffer. A second sample contained 6 grams SAP, 0.3 grams Chloramine-T and 0.5 grams sodium bicarbonate (buffer) was added (~4.4 wt % active compound). Human urine obtained from a person observing a coffee diet was used for testing.

One drop of human urine was initially applied to the SAP samples. Additional 2-50 more drops human urine were applied to the SAP samples for an eventual total of 350 (about 18 mL) drops per sample.

Results

As shown in the odor scale scores of Table 18 below, active formulation pre-treated SAP (with and without buffer) exhibited an immediate urine malodor reduction and maintained that malodor reduction even when more urine was added to the SAP. However, the pre-treated SAP maintained a low chlorine odor, which decreased upon increased urine application, while the control exhibited no chlorine odor and high urine malodor.

TABLE 18

| Odor | Control Sample size: 0.5 grams | First Sample (no buffer) | Second Sample (with buffer) |
|---|---|---|---|
| 1 drop human urine | | | |
| Urine Odor | 1 | 0 | 0 |
| Chlorine Odor | 0 | 1 | 1 |
| Additional 2 drops human urine (total of 3 drops) | | | |
| Urine Odor | 1 | 0 | 0 |
| Chlorine Odor | 0 | 1 | 1 |
| Additional 3 drops human urine (total of 6 drops) | | | |
| Urine Odor | 1 | 0 | 0 |
| Chlorine Odor | 0 | 1-2 | 1-2 |
| Mix | | | |
| Urine Odor | 2 | 0 | 0 |
| Chlorine Odor | 0 | 2 | 2 |
| Additional 6 drops human urine (total of 12 drops) | | | |
| Urine Odor | 2-3 | 0 | 0 |
| Chlorine Odor | 0 | 2-3 | 2-3 |
| Mix | | | |
| Urine Odor | 2-3 | 0 | 0 |
| Chlorine Odor | 0 | 2-3 | 2-3 |
| Additional 6 drops human urine (total of 18 drops) | | | |
| Urine Odor | 2-3 | 0 | 0 |
| Chlorine Odor | 0 | 2-3 | 2-3 |
| Mix | | | |
| Urine Odor | 2-3 | 0 | 0 |
| Chlorine Odor | 0 | 2-3 | 2-3 |
| Additional 12 drops human urine (total of 30 drops) | | | |
| Urine Odor | 3 | 0 | 0 |
| Chlorine Odor | 0 | 2 | 2 |
| Mix | | | |
| Urine Odor | 3 | 0 | 0 |
| Chlorine Odor | 0 | 3 | 3 |
| Additional 25 drops human urine (total of 55 drops) | | | |
| Urine Odor | 4 | 0 | 0 |
| Chlorine Odor | 2-3 | 2-3 | 0 |
| Mix | | | |
| Urine Odor | 4 | 0 | 0 |
| Chlorine Odor | 2-3 | 2-3 | 0 |
| Additional 25 drops human urine (total of 80 drops) | | | |
| Urine Odor | 4 | 0 | 0 |
| Chlorine Odor | 0 | 2-3 | 2-3 |
| Additional 20 drops human urine (total of 100 drops) | | | |
| Urine Odor | 5 | 0 | 0 |
| Chlorine Odor | 0 | 2 | 2 |

TABLE 18-continued

| Odor | Control Sample size: 0.5 grams | First Sample (no buffer) | Second Sample (with buffer) |
|---|---|---|---|
| Additional 25 drops human urine (total of 125 drops) | | | |
| Urine Odor | 5+ | 0 | 0 |
| Chlorine Odor | 0 | 1-2 | 1-2 |
| Additional 25 drops human urine (total of 150 drops) | | | |
| Urine Odor | 5-6 | 0 | 0 |
| Chlorine Odor | 0 | 1+ | 1+ |
| Additional 50 drops human urine (total of 200 drops) | | | |
| Urine Odor | 6 | 0 | 0 |
| Chlorine Odor | 0 | 1+ | 1+ |
| Mix | | | |
| Urine Odor | 6 | 0-1 | 0-1 |
| Chlorine Odor | 0 | 2 | 2 |
| Additional 50 drops human urine (total of 250 drops) | | | |
| Urine Odor | 5 | 0 | 0 |
| Chlorine Odor | 0 | 1 | <0.5 |
| Additional 50 drops human urine (total of 300 drops) | | | |
| Urine Odor | 5-6 | 0 | 1 |
| Chlorine Odor | 0 | 1 | <0.5 |
| Additional 50 drops human urine (total of 350 drops) | | | |
| Urine Odor | 5-6 | 0 | 1-2 |
| Chlorine Odor | 0 | <0.5 | 0 |
| Mix | | | |
| Urine Odor | 6 | 1-2 | 2-3 |
| Chlorine Odor | 0 | 0 | 0 |
| After 50 minutes | | | |
| Urine Odor | 6 | <1 | 2 |
| Chlorine Odor | 0 | 0 | 0 |

Example 18

Materials and Methods 0.06 grams dry Chloramine-T was applied to 6 grams super absorbent polymer (SAP) (~1.0 wt % active compound, 0.01 grams active compound per gram of SAP) with no buffer. In a separate sample, 0.06 grams of dry BENZ was applied to 6 grams SAP. Human urine was used for testing.

Ten drops of human urine were initially applied to the SAP samples. Additional 10-20 drops of human urine were applied periodically to the SAP samples for an eventual total of 200 drops per sample.

Results

As shown in the odor scale scores of Table 19 below, both chloramine-T and BENZ worked well in reducing the odor. The treated SAP samples both maintained a low chlorine odor, while the control exhibited no chlorine odor and high urine malodor.

TABLE 19

| Odor | Control Sample size: 0.5 grams | Chloramine-T Sample size: 0.5 grams | BENZ Sample size: 0.5 grams |
|---|---|---|---|
| 10 drops human urine | | | |
| Urine Odor | 2 | 0 | |
| Chlorine Odor | 0 | 1 | |
| Additional 10 drops human urine (total of 20 drops) | | | |
| Urine Odor | 2 | 0 | |
| Chlorine Odor | 0 | <1 | |

TABLE 19-continued

| Odor | Control Sample size: 0.5 grams | Chloramine-T Sample size: 0.5 grams | BENZ Sample size: 0.5 grams |
|---|---|---|---|
| Additional 10 drops human urine (total of 30 drops) | | | |
| Urine Odor | 2-3 | 0 | 0 |
| Chlorine Odor | 0 | <1 | <1 |
| Mix | | | |
| Urine Odor | 2-3 | 0 | |
| Chlorine Odor | 0 | <1 | |
| Additional 10 drops human urine (total of 40 drops) | | | |
| Urine Odor | 3 | 0 | |
| Chlorine Odor | 0 | 1 | |
| Mix | | | |
| Urine Odor | 3 | 0 | |
| Chlorine Odor | 0 | 1+ | |
| Additional 20 drops human urine (total of 60 drops) | | | |
| Urine Odor | 3+ | 0 | 0 |
| Chlorine Odor | 0 | 1 | <1 |
| Mix | | | |
| Urine Odor | 3-4 | 0 | |
| Chlorine Odor | 0 | 1+ | |
| Additional 20 drops human urine (total of 80 drops) | | | |
| Urine Odor | 4 | 0 | |
| Chlorine Odor | 0 | 1 | |
| Additional 20 drops human urine (total of 100 drops) | | | |
| Urine Odor | 4 | 0 | 0 |
| Chlorine Odor | 0 | <1 | <0.5 |
| Additional 20 drops human urine (total of 120 drops) | | | |
| Urine Odor | 5 | 0 | |
| Chlorine Odor | 0 | <0.5 | |
| Additional 20 drops human urine (total of 140 drops) | | | |
| Urine Odor | 5+ | 1 | |
| Chlorine Odor | 0 | <0.5 | |
| Additional 20 drops human urine (total of 160 drops) | | | |
| Urine Odor | 5 | 1 | |
| Chlorine Odor | 0 | 0 | |
| Additional 20 drops human urine (total of 180 drops) | | | |
| Urine Odor | 5 | 1 | |
| Chlorine Odor | 0 | 0 | |
| Additional 20 drops human urine (total of 200 drops) | | | |
| Urine Odor | 5 | 1+ | 1 |
| Chlorine Odor | 0 | 0 | <<0.5 |

Example 19

Materials and Methods

Adult incontinence products were evaluated for odor control. Depends® for Women (size S/M) and Depends® Silhouettes were non-fragranced products. Always® Discreet was a fragranced underwear version. The sides of all products were cut so that the products would lay flat. The topsheets of the treated products were cut and folded back so that the top part of the absorbent material (core) could be sprayed evenly with a solution of 1% BENZ and 0.5% sodium bicarbonate buffer. 120 sprays were applied and allowed to air dry. The total amount of active compound over the surface area of the core was 0.156 grams active per gram of absorbent material. The topsheet was placed back over the core and the urine specimen was applied to the topsheet. The urine specimen was collected at first morning void (overnight urine) from female on asparagus diet. 150 mL of urine was applied to each test product.

Results

As shown in the odor scale scores of Table 20 below, the treated samples had a much lower odor, both compared to their original odor and compared to the untreated samples at each time point.

TABLE 20

| Time (min.) | Depends ® Women | | Always ® Discreet | | Depends ® Silhouettes | |
|---|---|---|---|---|---|---|
| | Untreated | Treated | Untreated | Treated | Untreated | Treated |
| 0.5 | 7 | 5 | 7 | 6 | 6 | 4 |
| 1.5 | 7 | 4 | 6.5-7 | 3 | 6 | 3 |
| 3 | 6.5-7 | 3.5 | 6.5-7 | 3 | 6 | 2 |
| 7 | 6.5 | 3 | 6.5 | 2-2.5 | 5.5 | 2 |
| 10 | 6-6.5 | 2-2.5 | 6-6.5 | 1 | 5.5 | 2 |
| 30 | 6-6.5 | 1.5-2 | 6 | 0-0.5 | 5.5 | <2 |
| 1440 | 6-6.5 | 2 | 6.5-7 | 0.5 | 6 | 1 |

Example 20

Materials and Methods

The test of Example 19 was performed for a longer time period.

Depends® for Women (size S/M) was a non-fragranced product. Always® Discreet was a fragranced product. The sides of all products were cut so that the products would lay flat. The topsheets of the treated products were cut and folded back so that the top part of the absorbent material (core) could be sprayed evenly with a solution of 1% BENZ and 0.5% sodium bicarbonate buffer. 120 sprays were applied and allowed to air dry. The total amount of active compound over the surface area of the core was 0.156 grams active compound per product. For an absorbent core of about 16.8 grams, this results in 0.009 grams of active compound per gram of absorbent core. For an absorbent core of about 19.2 grams, this results in 0.008 grams of active compound per gram of absorbent core. The topsheet was placed back over the core. As another test, on one of the Always® Discreet products, the 1% BENZ solution was sprayed on the topsheet, but not on the core. The urine specimen was collected at first morning void (overnight urine) from female on asparagus diet. 150 mL of urine was applied to the top sheet of each test product.

Results

As shown in the odor scale scores of Table 21 below, the treated samples had a much lower odor, both compared to their original odor and compared to the untreated samples at each time point out to 3 days. Application to the core and to the topsheet was equally effective in odor reduction. The odor of the treated products was approximately 25% that of the untreated products even after 3 days.

TABLE 21

| Time (min.) | Depends ® Women | | Always ® Discreet | | |
|---|---|---|---|---|---|
| | | | | Core | Topsheet |
| | Untreated | Treated | Untreated | Treated | Treated |
| 0.5 | 8 | 2.5 | 7 | 4 | 3 |
| 1-2 | 7 | 2 | 7 | 3 | 2 |
| 3 | 6.5 | 1.5 | 6 | 2.5 | 1.5 |
| 7 | 6.5 | 1-1.5 | 6 | 1.5 | 1.5 |
| 10 | 6 | 1 | 6 | 1.5 | 1 |
| 60 | 6 | 1.5 | 6 | 1.5 | 1 |
| 90 | 7 | 2 | | | |
| 150 | 7 | 2.5-3 | 6.5 | 1.5 | 1.5 |

TABLE 21-continued

| Time (min.) | Depends ® Women | | Always ® Discreet | | |
|---|---|---|---|---|---|
| | | | | Core | Topsheet |
| | Untreated | Treated | Untreated | Treated | Treated |
| 4320 (3 days) | 7-8 | 2 | 7 | 1 | 0.5-1 |

Example 21

Materials and Methods

Always® Ultra Thin Pad (Long Super) and U by Kotex® (Ultra Thin Long) pads were evaluated for odor control with menses. The control products were untreated. For the treated products, the topsheet of the pads were cut and folded back to expose the absorbent material (core). The test products were treated with 7 sprays of a formulation containing 5% BENZ and 0.75% sodium bicarbonate, sprayed evenly over the core, for a total of about 0.045 grams active compound per feminine pad. The core (absorbent material) of the pad was about 5 grams, so there was about 0.009 grams of active compound per gram of absorbent material. The cores were allowed to air dry. The topsheet was secured back over the core in preparation for use.

Panelists alternated between using control pads and treated pads during their menstrual cycle.

Results

Results are shown in FIG. 6. As seen there, the treated samples had a lower odor compared to the untreated samples. The odors were lower on the Kotex® pads whether treated or untreated. The results indicated that the sulfonamide compound would also reduce the odor of menses (not just urine).

Example 22

Materials and Methods

Three non-fragranced training pet pads were used as test products. One pad was the control, and was not modified. A second non-fragranced pad was sprayed with Nature's Miracle®, a commercially available odor control product. The third non-fragranced pad was sprayed with a formulation (FBT) containing 0.75% BENZ and 0.15% chloramine-T. The total amount of active sulfonamide compound on the tested substrate was about 0.07 grams. For these two spray treated products, the non-woven topsheet was lifted back, so that the test product could be sprayed evenly onto the absorbent material. The products were allowed to air dry for 24+ hours. The topsheets were then replaced over the absorbent material. A fourth test product was a Nature's Miracle® fragranced pet pad. All four pads were tested by applying mink urine to the topsheet and evaluating the odor over time. Each drop of mink urine was approximately 0.02 grams in weight.

Results

Results are shown in Table 22 and in FIG. 7. The three treated pads displayed odor reduction compared to the control. However, only the pad sprayed with the active sulfonamide compound maintained the odor reduction over time.

TABLE 22

| Time (min.) | Control | Example (FBT) | Nature's Miracle Sprayed | Nature's Miracle Fragranced Pad |
|---|---|---|---|---|
| 0 | 9 | 9 | 9 | 9 |
| 0.5 | 9 | 4 | 6 | 3.5 |
| 2 | 8.5 | 3 | 4 | 2.5 |
| 5 | 5.5 | 2 | 5 | 5 |
| 15 | 8 | 2 | 7 | 6 |

Example 23

Materials and Methods

Three drops of undiluted mink urine was applied to each of three beakers. Each drop was about 0.02 grams in weight. One spray of ODOGard® Odor Eliminator (i.e. the FBT formulation) was applied to one beaker. The spray delivered about 1.25 to 1.35 ml of total formulation, resulting in about 0.01 grams of total active sulfonamide compound. One spray of Nature's Miracle® 3 in 1 Odor Destroyer was applied to a second beaker. A control beaker was not treated. Odor was evaluated over time. Each drop was about 0.02 grams in weight.

Results

Results are shown in Table 23 and in FIG. 8. Only the ODOGard® Odor Eliminator eliminated the odor, and maintained the odor reduction for 2 days.

It is believed that the Nature's Miracle® product combines both masking fragrances with enzymes. When first applied to the urine, the fragrance intensity is so high that it is difficult to detect the urine odor. As the fragrance goes away, the underlying urine odor, which was always there, becomes detectable. Additionally, the enzymatic approach to neutralizing odor-causing molecules takes longer. In contrast, the ODOGard® containing the active sulfonamide compound works quickly and over long periods of time. This quickly eliminates the odor-causing molecules so they cannot be smelled.

TABLE 23

| Time (min.) | Control | Example (FBT) | Nature's Miracle 3-in-1 Odor Destroyer |
|---|---|---|---|
| 0 | 10 | 4 | 1 |
| 0.25 | 9 | 2 | 4 |
| 0.5 | 9 | 0 | 5 |
| 1 | 9 | 0 | 5 |
| 2880 (2 days) |  | 0 | 5 |

Example 24

Materials and Methods

The experiment of Example 23 comparing ODOGard® Odor Eliminator with Nature's Miracle® 3 in 1 Odor Destroyer was repeated for a longer time period. Three drops of undiluted mink urine were applied to a hard surface, and the two odor-controlling compositions were sprayed once onto the urine. 15 minutes later, a second spray was applied to the urine. Each spray of ODOGard® Odor Eliminator (i.e. the FBT formulation) delivered about 1.25 to 1.35 ml of total formulation, resulting in a total applied formulation amount of about 2.5 to 2.7 ml and a total amount of about 0.02 grams of active sulfonamide compound.

Results

Results are shown in Table 24. Again, the ODOGard® Odor Eliminator eliminated the odor, performing better than Nature's Miracle® at all times. The ODOGard® Odor Eliminator also maintained the odor reduction better for 2 days.

TABLE 23

| Time (min.) | Example (FBT) | Nature's Miracle 3-in-1 Odor Destroyer |
|---|---|---|
| First Spray | | |
| 0 | 5 | 5 |
| 1 | 4 | 6 |
| 2 | 3 | 7 |
| 3.5 | 2 | 8 |
| 5 | 2 | 8 |
| 11 | 2 | 7 |
| 15 | 2 | 7 |
| Second Spray | | |
| 16 | 1 | 5 |
| 17 | 1 | 6 |
| 18 | 1 | 6-7 |
| 20 | 1 | 7 |
| 21 | 0-1 | 7 |
| 24 | 0-1 | 7 |
| 26 | 0-1 | 7 |
| 2880 (2 days) | 0 | 8 |

DISCUSSION

As seen in the Examples, the use of the active sulfonamide compound reduces, and often eliminates, urine malodors. These compounds were effective at very low concentrations on a wide variety of articles, including cores, topsheets, and SAP. This high rate of success indicates that the active formulations may be applied to a wide variety of other materials, including adhesives, backsheets, and fluff.

Using a ratio of about 0.1-1 mg active compound per 1 mL urine, urine malodor was significantly reduced, indicating that lower concentrations of such a composition are still efficient. The addition of a buffer was not necessary to achieve this effect. However, buffers are helpful for combating odors from very acidic urine because they prevent the active compound from being deactivated due to acidic pH.

In addition, the sulfonamide compounds reduced odor over long periods of time, i.e. days and weeks, as seen in many of the Tables. By treating articles with such compositions, odor may be severely reduced or eliminated until time for permanent disposal can be made.

As shown in Tables 17-19, super absorbent polymer (SAP) can be treated with aqueous or solid forms of the active sulfonamide compound.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An odor-controlling article, comprising:
    an absorbent substrate having thereon a halo active aromatic sulfonamide compound of Formula (I):

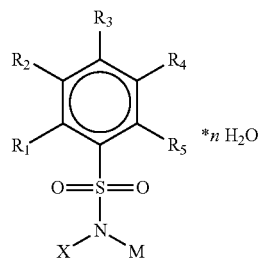

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound;
    wherein the halo active aromatic sulfonamide compound is present in the amount of about 0.0002 to about 6 milligrams per milliliter (mg/mL) of absorbent capacity of the absorbent substrate; and
    wherein the halo active aromatic sulfonamide compound is a solid or is encapsulated in a water-soluble shell.

2. The article of claim 1, wherein the halo active aromatic sulfonamide compound is present in the amount of about 0.0002 to about 1 mg/mL of absorbent capacity of the absorbent substrate.

3. The article of claim 1, wherein the halo active aromatic sulfonamide compound is present in the amount of about 0.1 to about 1 mg/mL of absorbent capacity of the absorbent substrate.

4. The article of claim 1, wherein $R_3$ is substituted or unsubstituted $C_1$-$C_{12}$ alkyl, or is COOR', wherein R' is an alkali metal, an alkaline earth metal, substituted $C_1$-$C_{12}$ alkyl, or unsubstituted $C_1$-$C_{12}$ alkyl.

5. The article of claim 1, wherein the halo active aromatic sulfonamide compound is N-chloro-4-carboxybenzenesulfonamide.

6. The article of claim 1, wherein the absorbent substrate also includes a buffering agent thereon.

7. The article of claim 6, wherein the buffering agent is sodium bicarbonate.

8. The article of claim 6, wherein the weight ratio of the halo active aromatic sulfonamide compound to the buffering agent is from about 50:1 to about 1:1.

9. The article of claim 6, wherein the buffering agent is present in a quantity sufficient to obtain a pH of 7.0 to 9.0 when the absorbent substrate is wetted.

10. The article of claim 1, wherein the article further comprises an alcohol, a surfactant, or a fragrance.

11. The article of claim 1, wherein the absorbent substrate is made from a polymer, a non-woven material, cellulosic fiber, or wood fluff.

12. The article of claim 1, wherein the article is a diaper, an adult incontinence article, a feminine pad, pet pad, food pad, or other absorbent pad.

13. The article of claim 1, containing a total of about 10 mg to about 1000 mg of the halo active sulfonamide compound.

14. The article of claim 1, wherein the halo active aromatic sulfanomide compound is a solid, and the absorbent substrate is a super absorbent polymer.

15. A wipe, comprising:
    a non-woven material having thereon a halo active aromatic sulfonamide compound of Formula (I):

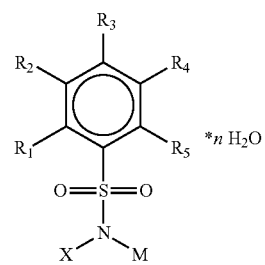

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound;
    wherein the halo active aromatic sulfonamide compound is present in the amount of about 0.001 to about 1.0 grams per gram of the non-woven material; and
    wherein the halo active aromatic sulfonamide compound is a solid or is encapsulated in a water-soluble shell.

16. A method of reducing odor for a time period of at least 168 hours, comprising:
    receiving an odorous liquid in an article comprising:
        an absorbent member having thereon a halo active aromatic sulfonamide compound of Formula (I):

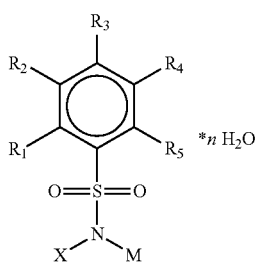

Formula (I)

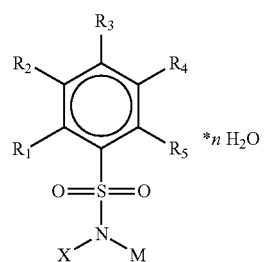

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted C$_1$-C$_{12}$ alkyl;

R' is hydrogen, an alkali metal, an alkaline earth metal, substituted C$_1$-C$_{12}$ alkyl, or unsubstituted C$_1$-C$_{12}$ alkyl; and R" is hydrogen or substituted or unsubstituted C$_1$-C$_{12}$ alkyl, where the two R" groups in CON(R")$_2$ may be independently selected;

X is halogen;

M is an alkali or alkaline earth metal; and n is the number of water molecules per molecule of the sulfonamide compound;

wherein the halo active aromatic sulfonamide compound is present in the amount of about 0.0002 to about 6 milligrams per milliliter (mg/mL) of absorbent capacity of the absorbent member; and wherein the halo active aromatic sulfonamide compound is a solid or is encapsulated in a water-soluble shell.

17. The method of claim 16, wherein the odor of the liquid is at most 40% of the original odor after one week.

18. A filter or other medium, comprising:
a substrate having thereon a halo active aromatic sulfonamide compound of Formula (I):

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted C$_1$-C$_{12}$ alkyl;

R' is hydrogen, an alkali metal, an alkaline earth metal, substituted C$_1$-C$_{12}$ alkyl, or unsubstituted C$_1$-C$_{12}$ alkyl; and R" is hydrogen or substituted or unsubstituted C$_1$-C$_{12}$ alkyl, where the two R" groups in CON(R")$_2$ may be independently selected;

X is halogen;

M is an alkali or alkaline earth metal; and n is the number of water molecules per molecule of the sulfonamide compound;

wherein the halo active aromatic sulfonamide compound is present in the amount of about 0.001 to about 1.0 grams per gram of the substrate; and wherein the halo active aromatic sulfonamide compound is a solid or is encapsulated in a water-soluble shell.

19. The article of claim 1, wherein the halo active aromatic sulfonamide compound is encapsulated in a water-soluble shell.

* * * * *